United States Patent [19]

Clark et al.

[11] Patent Number: 5,202,119
[45] Date of Patent: Apr. 13, 1993

[54] METHOD OF STIMULATING IMMUNE RESPONSE

[75] Inventors: Ross G. Clark, Pacifica; Paula M. Jardieu, Berkeley, both of Calif.

[73] Assignee: Genentech, Inc., South San Francisco, Calif.

[21] Appl. No.: 722,813

[22] Filed: Jun. 28, 1991

[51] Int. Cl.$^5$ .................. A61K 37/26; A61K 39/00; A61K 37/36
[52] U.S. Cl. .......................................... 424/88; 514/3
[58] Field of Search .............................. 424/88; 514/3

[56] References Cited

U.S. PATENT DOCUMENTS 4,837,202 6/1989 Edwards et al. .

FOREIGN PATENT DOCUMENTS

WO89/05822 6/1989 PCT Int'l Appl. .

OTHER PUBLICATIONS

Kelley, Psychoneuroimmunology, 2nd Ed., Ader et al., eds., Academic Press, Inc. (1991) pp. 377–402.
Kiess et al., Clin. Immunol. & Immunopath., 48:85–94 (1988).
Pandian & Talwar, J. Exp. Med., 134:1095–1113 (1971).
Gupta et al., Clin. Exp. Immunol., 54:87–90 (1983).
Savino et al., Clin. Exp. Immun., 52:1–6 (1983).
Rapaport et al., J. Pediatr., 109(3): 434–439 (1986).
Bozzola et al., Acta Poediatr. Scand., 77: 675–680 (1988).
Rapaport et al., Life Sciences, 41:2319–2324 (1987).
Verland and Gammeltoft, Mol. & Cell. Endocr., 67:207–216 (1989).
Johnson & Kozak, Endocr. Soc. 73rd Ann. Mtg., abstr. #1073, p. 299, Jun. 19–22, 1991.
Timsit et al., Endocr. Soc. 73rd Am. Mtg., abstr. #1296, p. 354, Jun. 19–22, 1991.
Baroni, Experimentia, 23(4):282–283 (1967).
Roth et al., Am. J. Vet. Res., 45(6):1151–1155 (1984).
Schimpff et al., Acta Endocr., 102:21–26 (1983).
Fabris et al., Clin. Exp. Immunol., 9:209–225 (1971).
Baroni et al., Immunol., 17:303–314 (1969).
Rom et al., J. Clin. Invest., 82:1685–1693 (1988).
Murphy et al., Endocr., 120(4):1279–1282 (1987).
Merimee et al., J. Clin. Endocr. & Metab., 69(5):978–984 (1989).
Merchav et al., J. Clin. Invest., 81:791–797 (1988).
Kozak et al., Cellular Immunol., 109:318–331 (1987).
Kelley, Biochem. Pharmacol., 38(5):705–713 (1989).
Fu et al., J. Immunol., 146(5):1602–1608 (1991).
Marsh et al., Proc. of Soc. for Exp. Biol. & Med., 175:351–360 (198).
Pierpaoli & Sorkin, Nature, 215:834–838 (1967).
Murphy et al., FASAB Mtg. Abstr., Atlanta, Apr. 1991.
Durum et al., FASAB Mtg. Abstr., Atlanta, Apr. 1991.
Stuart et al., J. Clin. Endocr. & Metab., 72(5):1117–1122 (1991).
Guler et al., PNAS USA, 85:4889–4893 (1988).
Ammann, in Human Growth Hormone, Progress and Challenges, Underwood, ed., Marcel Dekker, NY (1988) pp. 243–253.
DePasquale-Jardien & Fraker, J. Immunol., 124(6):2650–2655 (1980).
Goff et al., Clin, Exp. Immun., 68:580–587 (1987).
Geffner et al., J. Clin. Endocr. Metab., 71(2):464–469 (1990).
Tapson et al., J. Clin. Invest., 82:950–957 (1988).
Franco et al., Acta Endocrin., 123:339–344 (1990).

(List continued on next page.)

Primary Examiner—Merrell C. Cashion, Jr.
Assistant Examiner—Choon Koh
Attorney, Agent, or Firm—Janet E. Hasak

[57] ABSTRACT

A method is disclosed for stimulating a mammal's or avian's immune response, particularly immune-compromised mammals, by administration of IGF-I, alone or in combination with growth hormone. Preferably, the IGF-I is native-sequence, mature human IGF-I.

16 Claims, 26 Drawing Sheets

OTHER PUBLICATIONS

Hunt & Eardley, J. Immunol., 136(11):3994-3999 (1986).

Weigent & Blalock, Progress in NeuroEndocrinImmunology, 3(4):231-241 (1990).

Froesch et al., in Growth Hormone-Basic and Clinical Aspects, Isaksson et al., eds., Excerpta Medica, Amsterdam, pp. 321-336 (1987).

Binz et al., PNAS USA, 87:3690-3694 (1990).

Kurtz et al., PNAS USA, 85:7825-7829 (1988).

Timsit et al., C. R. Acad. Sci., 310:7-13 (1990).

Schwartz et al., AJDC, 145:330-333 (1991).

Swanson, Perspectives in Biology & Medicine, 33(2):157-186 (1990).

Saenger, Serono Symposia Publications, Growth Disorders: The State of the Art, 81:127-136 (1991) (Raven Press).

Salbe et al., Clin. Res., 39(2):385A (1991).

Rapaport et al., Ped. Res., 25(4 pt. 2): 187A (1989).

Schwartz et al., Ped. Res., 25(4 pt. 2): 136A (1989).

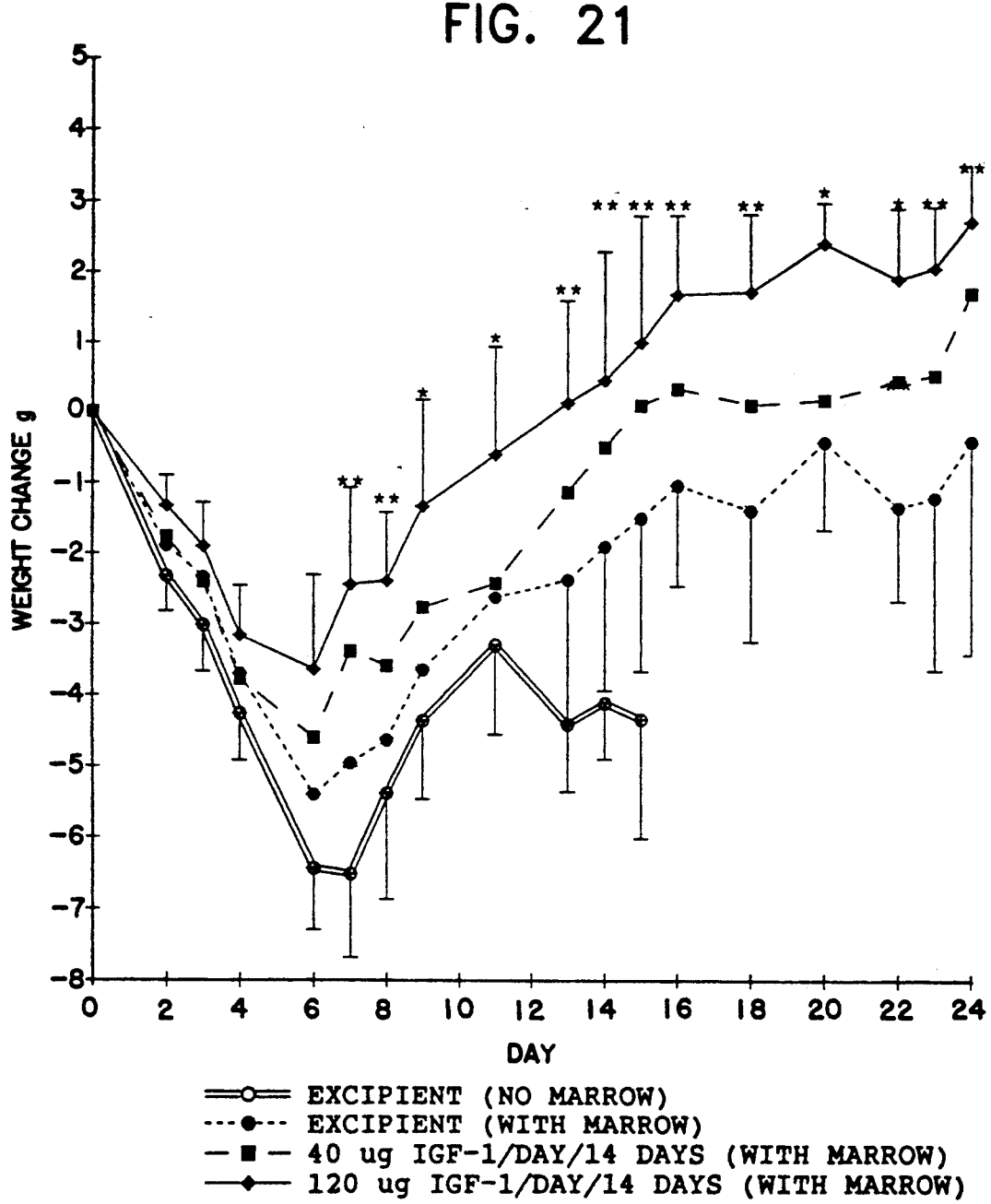

METHOD OF STIMULATING IMMUNE RESPONSE

BACKGROUND OF THE INVENTION

1. Field of the Invention

This invention relates to a method of stimulating immune response in mammals or avian, including increasing antibody response to antigens in patients with depressed immune systems.

2. Description of Related Art

Insulin-like growth factor I (IGF-I) is a polypeptide naturally occurring in human body fluids, for example, blood and human cerebral spinal fluid. Most tissues, and especially the liver, produce IGF-I together with specific IGF-binding proteins. IGF-I production is under the dominant stimulatory influence of growth hormone (GH), and some of the IGF-I binding proteins are also increased by GH. See Tanner et al., *Acta Endocrinol.,* 84:681-696 (1977); Uthne et al., *J. Clin. Endocrinol. Metab.,* 39:548-554 (1974)). IGF-I has been isolated from human serum and produced recombinantly. See, e.g., EP 123,228 and 128,733.

Human growth hormone (hGH) is a single-chain polypeptide consisting of 191 amino acids (molecular weight 21,500). Disulfide bonds link positions 53 and 165 and positions 182 and 189. Niall, *Nature, New Biology.* 230:90 (1971). hGH is a potent anabolic agent, especially due to retention of nitrogen, phosphorus, potassium, and calcium. Treatment of hypophysectomized rats with GH can restore at least a portion of the growth rate of the rats. Moore et al., *Endocrinology,* 122:2920-2926 (1988). Among its most striking effects in hypopituitary (GH-deficient) subjects is accelerated linear growth of bone growth plate cartilage resulting in increased stature. Kaplan, *Growth Disorders in Children and Adolescents* (Springfield, Ill.: Charles C. Thomas, 1964).

It has been reported that, especially in women after menopause, GH secretion declines with age. Millard et al., *Neurobiol. Aging,* 229-235 (1990); Takahashi et al., *Neuroendocrinology,* 46:137-142 (1987). See also Rudman et al., *J. Clin. Invest.,* 67:1361-1369 (1981) and Blackman, *Endocrinology and Aging,* 16:981 (1987). Moreover, a report exists that some of the manifestations of aging, including decreased lean body mass, expansion of adipose-tissue mass, and the thinning of the skin, can be reduced by GH treatment three times a week. See, e.g., Rudman et al., *N. Eng. J. Med.,* 323:1-6 (1990) and the accompanying article in the same journal issue by Dr. Vance (pp. 52-54).

The levels of IGF-I are reported to be reduced by half in 20-month old rats compared to 6-month old rats. Takahashi and Meiters, *Proc. Soc. Exp. Biol. Med.,* 186:229-233 (1987). See also Florini and Roberts, *J. Gerontol.,* 35:23-30 (1980); Florini et et al., *Mech. Aging Dev.,* 15:165-176 (1981); Chatelain et al., *Pediatrie,* 44:303-308 (1989); Florini et al., *J. Gerontol.,* 40:2-7 (1985); Hall and Sara, *Clinics in Endocrin, and Metab.,* 15:629 (1984); Baxter, *Advances in Clinical Chemistry,* 25:49 (1986); Clemmons and Underwood, *Clinics in Endocrin. and Metab.,* 28:629 (1986); Hintz, *Advances in Pediatrics,* 28:293 (Year Book Medical Publishers, Inc., 1981); Johanson and Blizzard, *The Johns Hopkins Medical Journal,* 149:115-117 (1981), the latter five references describing low IGF-I levels in aged men. The Hintz, Clemmons and Underwood, and Baxter references are general reviews on IGF-I.

Furthermore, it was found that among human diploid fibroblasts capable of cycling in aging cultures in vitro, there were few changes in the regulation of the growth fraction by platelet-derived growth factor (PDGF) and epidermal growth factor (EGF), but a greatly increased dependence on IGF-I for regulation of the rate of entry into S phase. Chen and Rabinovitch, *J. Cell. Physiol.,* 144:18-25 (1990). The authors conclude that the slower growth of the dividing population of cells in aging cultures may be related to a requirement for IGF-I at levels that are greatly above those usually supplied. This may be due to overproduction of the IGF-I binding protein, IGFBP-3, and, therefore, a reduction in IGF-I availability to its receptor. Goldstein et al., "Cellular and Molecular Applications to Biology of Aging", AFCR Meeting abstract, Seattle, May 4-5, 1991.

Various biological activities of IGF-I in other than aged mammals have been identified. For example, IGF-I is reported to lower blood glucose levels in humans. Guler et al, *N. Engl. J. Med.,* 317:137-140 (1987). Additionally, IGF-I promotes growth in several metabolic conditions characterized by low IGF-I levels, such as hypophysectomized rats [Skottner et al., *J. Endocr.,* 112:123-132 (1987)], diabetic rats [Scheiwiller et at., *Nature,* 323:169-171 (1986)], and dwarf rats.[Skottner et al., *Endocrinology,* 124:2519-2526 (1989)]. The kidney weight of hypophysectomized rats increases substantially upon prolonged infusions of IGF-I subcutaneously. Guler et al., *Proceedings of the 1st European Congress of Endocrinology,* 103: abstract 12-390 (Copenhagen, 1987). The kidneys of Snell dwarf mice and dwarf rats behaved similarly. van Buul-Offers eg al., *Pediatr. Res,* 20:825-827 (1986); Skottner et al. *Endocrinology,* supra. An additional use for IGF-I is to improve glomerular filtration and renal plasma flow. Guler et al., *Proc. Natl. Acad. Sci. USA,* 86: 2868-2872 (1989). The anabolic effect of IGF-I in rapidly growing neonatal rats was demonstrated in vivo. Philipps et al., *Pediatric Res.,* 23:298 (1988). In underfed, stressed, ill, or diseased animals, IGF-I levels are well known to be depressed.

GH and IGF-I have been linked with immunoregulatory properties. The immune response results from interaction of antigens (foreign or non-self moieties) with host cells (lymphocytes) bearing specific receptors on the surface membrane for these antigens. Lymphocytes are grouped into two major classes, T-cells and B-cells.

T-cells originate from the thymus where they mature and differentiate from bone-marrow-derived cells. The mature T-cells leave the thymus gland to continuously circulate from blood to lymph nodes and spleen and back to blood. T-cells are further subdivided into three major subsets: T-helper cells, T-suppressor cells, and T-cytolytic cells. T-helper cells "help" other cells: B-cells to secrete antibody, cytotoxic cells to become functional, and macrophages to become activated. This population of T-cells bears the $CD_4$ surface marker that is used to identify this subset in tissue and blood.

T-cytolytic cells are responsible for killing target cells such as virally infected cells, tumor cells, and allografts. Suppressor T-cells act to limit and terminate the immune response. The cytolytic and suppressor T-cell populations are identified by the $CD_8$ surface marker.

The B-cells, or antibody-forming cells, also derive from immature precursors found in the bone marrow. When mature, the B-cells migrate to all lymphoid organs except the thymus. B-cells interact with antigens by way of antibody molecules bound to their plasma membranes that act as receptor proteins. This surface immunoglobulin is used as a marker to identify B-cells in tissue and blood. Following interaction with antigen and T-helper cells, the B-cells differentiate into antibody-forming cells called plasma cells. These plasma cells secrete antibody into the extracellular matrix. The antibody diffuses into capillaries and circulates via normal blood flow. Thus, the serum immunoqlobulin level reflects the cellular dynamics of the immune response.

In many states, children are required to be immunized routinely against such diseases as diphtheria, pertussis, and typhoid (DPT), as well as measles, tetanus, mumps, polio, and rubella, by administering vaccines. The B-cell reaction to vaccine is the production of appropriate immunoglobulins, which are intended to confer immunity against the disease. Generally, a particular B-cell will be differentiated to produce one particular type of antibody, and such production is caused by the presence in the body of one particular type of antigen. Hence, when an animal or person has been exposed to a number of different antigens, the animal or human will have a number of different B-cells that can produce its particular immunoglobulins when the appropriate antigen is present.

In some situations, the immune response to antigen is insufficient to confer immunity. That is, a quantity of immunoglobulins is generated (or a number of B-cells are potentiated) that is insufficient to confer effective immunity.

It has been known since 1967 that a connection exists between the anterior pituitary and the immune system, and specifically with GH. Two groups of investigators concluded from their studies that GH controls the growth of lymphoid tissue. Pierpaoli and Sorkin, Nature, 215:834 (1967); Baroni, Experientia, 23:282 (1967). Subsequently, immunologic function was restored in the pituitary dwarf mouse by a combination of bovine somatotropic hormone and thyroxin. Baroni et al., Immunol., 17:303-314 (1969).

In a sex-linked dwarf chicken strain, bovine GH treatment resulted in enhanced antibody responses and bursal growth while thyroxine treatment stimulated thymus growth. Marsh et al., Proc. Soc. Exp. Biol. Med., 175:351-360 (1984). However, neither treatment altered immune function in the autosomal dwarf chicken. Bovine GH therapy alone partially restored immunologic function in immunodeficient Weimaraner dogs. Roth et al., Ann. J. Vet. Res., 45:1151-1155 (1984).

Mice with hereditary GH deficiency develop an impairment of the immune system associated with thymic atrophy, immunodeficiency, and wasting, resulting in a shortened life expectancy. Frabris et al., Clin. Exp. Immunol., 9:209-225 (1971). It has been shown that an age-associated decline in the plasma concentration of thymulin (a thymic hormone) occurs and that plasma thymulin concentration increases in bGH-treated middle-aged and old dogs. Goff et al., Clin. Exp. Immunol., 68:580-587 (1987). The authors suggest that exogenous GH may be useful for restoring some immune functions in aged individuals. Further, administration of hGH to $C_{57}/B1/6J$ mice was found to reverse the inhibitory effect of prednisolone on thymus and spleen cellularity and on natural killer activity; administration of hGH without prednisolone had no effect, although at higher doses it induced a decrease of thymic parameters and natural killer activity with no effect on spleen cellularity, and relative weights. Franco et al., Acta Endocrinologica, 123:339-344 (1990).

It has also been shown that GH induces T-cell proliferation in the thymus. Murphy et al., FASEB Meeting Abstract, Atlanta, April 1991; Durum et al., FASEB Meeting Abstract, Atlanta, April 1991. For recent reviews on the immune effects of GH, see Kelley, "Growth Hormone in Immunobiology," in Psychoneuroimmunology II, 2nd Ed., B. Ader et al., eds., Acad. Press 1990, and Ammann, "Growth Hormone and Immunity," in Human Growth Hormone--Progress and Challenges, L. Underwood, ed., Marcel Dekker, Inc., New York, (1988), pp. 243-253; Weigent and Blalock, Prog. NeuroEndocrinImmunology, 231-241 (1990). It has been reported that the activity of all major immune cell types, including T-cells, B-cells, natural killer (NK) cells and macrophages, can be altered by GH. Kelly, Biochem. Pharmacol., 38:705 (1989).

One report states that locally generated IGF-I mediates GH action on T-lymphocytes through the type I IGF receptor. Geffner et al., J. Clin. Endocrin, and Metab., 71:464 (1990). Also, Franco et al., on p. 343, speculate that some of the effects of hGH on the immune system occur via IGF-I. Timsit et al., 73rd Annual Meeting, Endocrine Society, June 19-22, 1991, abstract 1296, reports hGH and IGF I stimulate thymic hormone function.

There have been data published documenting the ability of cells of the immune system to produce IGF-I-like molecules. These include activated alveolar macrophages [Rom et al., J. Clin. Invest., 82:1685 (1988)], human B-lymphocytes transformed with Epstein-Barr virus [Merimee et al., J. Clin. Endocrin. Metab., 69:978 (1989)], spleen and thymus tissues through detection of mRNA for IGF-I [Murphy et al., Endocrinology, 120:1279 (1987)], and normal T-cells [Geffner et al., supra].

Data have also been presented suggesting that IGF-I produced locally in tissues such as the thymus or inflammatory sites might affect the growth and function of IGF-I-receptor-bearing T-lymphocytes. Tapson et al., J. Clin. Invest., 82:950-957 (1988).

A statistically significant increase in thymus and spleen weight of hypophysectomized rats infused for 18 days with IGF-I was observed as compared to control or treatment with GH. Froesch et al., in Growth Hormone Basic and Clinical Aspects. eds. O. Isaksson et al., p. 321-326 (1987). Also reported was an increased thymic tissue in young GH-deficient rats treated with IGF-I [Guler et al., Proc. Natl. Acad. Sci. USA, 85:4889-4893 (1988)] and an increase in the spleen of dwarf rats [Skottner et al., Endocrinology, supra]. Others have shown repopulation of the atrophied thymus in diabetic rats using either IGF-I or insulin; however, when the rats were immunized with bovine serum albumin (BSA) and boosted, serum anti-BSA antibodies showed no effect of insulin or IGF-I on the antibody response despite large effects on thymic and splenic size. Binz et al., Proc. Natl. Acad. Sci. (USA). 87:3690-3694 (1990). IGF-I was reported to stimulate lymphocyte proliferation (Johnson et al., Endocrine Society 73rd Annual Meeting, abstract 1073, June 19-22, 1991).

Furthermore, IGF-I was found to repopulate the bone marrow cavity with hematopoietic cells [Froesch et al., supra], stimulate erythropoiesis in hypophysectomized rats [Kurtz et al., Proc. Natl. Acad. Sci. (USA). 85:7825-7829 (1988)], and enhance the maturation of morphologically recognizable granulocytic and erythroid progenitors in suspension cultures of marrow cells. Merchav et al., *J. Clin. Invest.*, 81:791 (1988).

At nanomolar concentrations, IGF-I is a growth-promoting factor for lymphocytes. Schimpff et al., *Acta Endocrinol.*, 102:21-25 21-25 (1983). B-cells, but not T-cells, have recently be to possess receptors for IGF-I. Stuart et al., *J. Clinical Endo. and Met.*, 72:1117-1122 (1991). Also, IGF-I, as a chemotactic for resting and activated T-cells, stimulates an increase in thymidine incorporation into resting and activated T-cells. Normal T-cell lines show augmentation of basal colony formation in response to IGF-I. Geffner et al., supra. It is also stated on p. 955 of Tapson et al., *J. Clin. Invest.*, 82:950-957 (1988) that IGF-I produced locally in tissues such as the thymus or inflammatory sites might affect the growth and function of IGF-I receptor-bearing T lymphocytes. However, IGF-I is reported to suppress in a dose-dependent manner IL-2-induced proliferative responses and in vitro antibody responses of splenocytes. Hunt and Eardley, *J. Immunol.*, 136:3994-3999 (1986).

There is a need in the art to supply a reagent that will stimulate the immune system of a mammal or avian, whether the immune response is cell-mediated or antibody-mediated. There is a particular need for a reagent that will boost the antibody response of patients with compromised immune systems to antigens to which they are exposed. In view of the controversy in the art surrounding IGF-I, it is unclear what its effects would be in increasing immune function, as opposed to merely increasing size of organs involved in immune function such as the thymus and spleen, or in increasing the activity of T- or B-cells in vitro or in vivo.

It is therefore an object of the present invention to stimulate the immune response of a mammal or avian.

It is a particular object to increase production of immunoglobulins by increasing the number of immunoglobulin-producing cells and/or by increasing the amount of immunoglobulin produced by the individual immunoglobulin-producing cells in response to the predetermined immunogen.

It is a more particular object to increase antibody responses in patients with severely hampered immune systems, such as patients who receive bone marrow transplants or in AIDS patients.

These and other objects will be apparent to those of ordinary skill in the art.

SUMMARY OF THE INVENTION

Accordingly, the present invention provides a method for stimulating a mammal's or avian's immune system comprising administering to the mammal or avian an immune-stimulating effective amount of IGF-I.

In a more particular aspect, the invention provides a method for increasing a mammal's or avian's antibody response to an immunogen comprising administering to the mammal or avian the immunogen and an effective amount of IGF-I. Preferably, this administration is concurrent and is followed by boosts of immunogen at shortened intervals relative to if no IGF-I is given.

In another aspect, the invention provides co-administration of effective amounts of IGF-I and GH for stimulating the immune system.

In still another aspect, a method is provided of increasing the amount of immunoglobulin produced by B-cells of a human or other mammalian subject in response to an immunogen, where said subject suffers from a condition in which insufficient immunoglobulin production occurs, comprising administering to the subject an effective amount of IGF-I, the amount being effective to increase the production of immunoglobulin.

In a still further aspect, the invention provides a method of increasing the T-cell responsiveness in a human or other mammalian subject in response to an immunogen, where said subject suffers from a condition in which insufficient T-help or T-cytolytic activity occurs, comprising administering to the subject an effective amount of IGF-I, the amount being effective to increase the T-help or T-cytolytic activity.

In yet another aspect, the invention provides a method of treating an immune-deficient mammal or avian comprising:

(a) measuring the serum IGF-I level of the mammal; and (b) if the serum IGF-I level is below a normal level for that mammal or avian, administering to the mammal or avian an effective amount of IGF-I to restore immunity.

While recent studies in whole animals mentioned above have shown that IGF-I can cause increased spleen and thymus weights in GH-deficient animals, these studies have not progressed beyond describing a gross change in thymus and spleen size or in cell number. Other manipulations of the size of the spleen and thymus have been shown not to be associated with an effect on function. Jardieu and Fraker, *J. Immunol.* 124:2650-2655 (1980). Furthermore, the Binz et al. article cited above utilized a diabetic rat model where insulin and IGF-I would affect diabetes and therefore aid all tissues in the body, and IGF-I and insulin were found to have no functional effect on antibody titer.

In view of this art, the present invention represents an unexpected finding that not only are the spleen and thymus weights increased upon administration of IGF-I, but also the function of the thymus, spleen, or lymph nodes, as indicated by increased splenocyte number, splenic T-cell population number, splenic B-cell number, and their responses to mitogens in vitro. The increase in B-cell number and responsiveness is now shown to translate to increased production of antibody by these cells in response to an antigen. This method would be useful in treating patients having compromised immune systems such as AIDS patients, in whom increased antibody response to antigens would ward off, or decrease the severity of, infectious diseases and in whom vaccines could be made more effective. Wherever IGF-I is used, it is reasonable to expect that IGF-II will similarly function.

BRIEF DESCRIPTION OF THE DRAWINGS

FIG. 21 shows the weight gain changes for mice with and without transplanted bone marrow and treated with excipient or 40 $\mu g$ or 120 $\mu g$ of IGF-I.

DESCRIPTION OF THE PREFERRED EMBODIMENTS

A. Definitions

Figure 1:
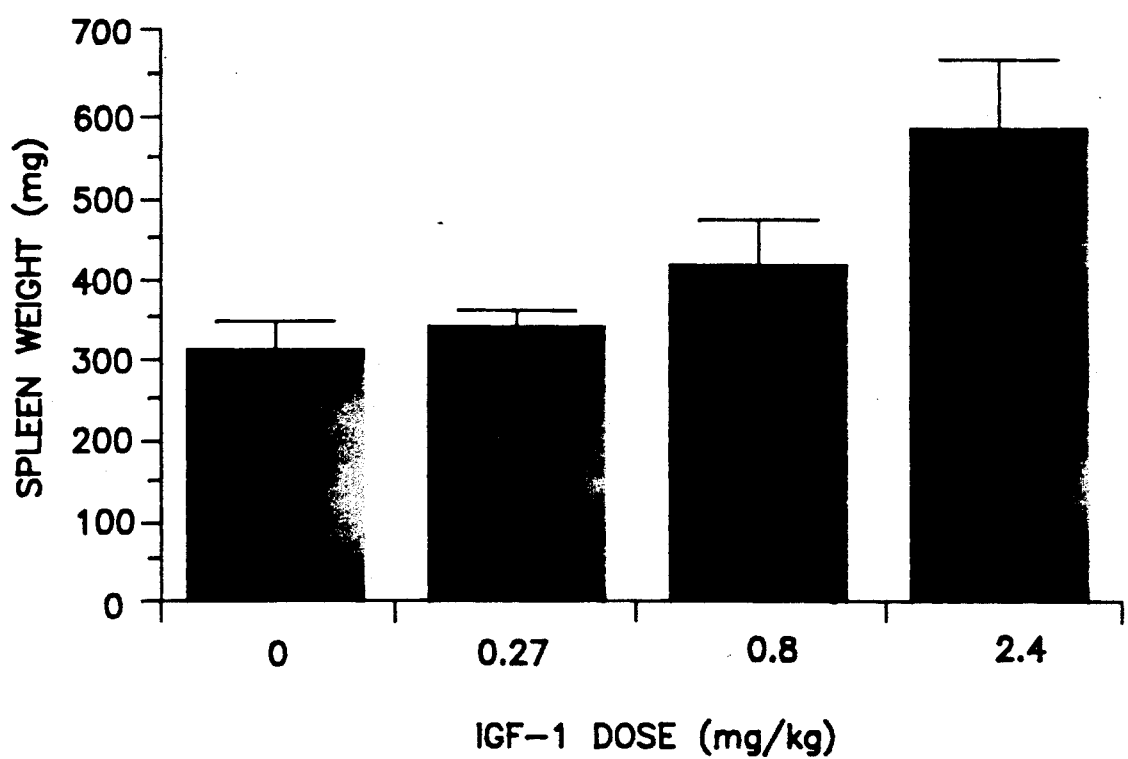
FIG. 1 is a graph of spleen weight of dwarf rats after 7 days of various doses of IGF-I administered by minipump.

As used herein, "stimulating an immune system" refers to increasing the immune function of a mammal or avian, whether the increase is due to antibody mediation or cell mediation, and whether the immune system is endogenous to the host treated with IGF-I or is transplanted from a donor to the host recipient given IGF-I (such as bone marrow transplants). For example, the stimulation may result from an increased number of splenic cells such as splenic lymphocyte number, splenic T-cell population number (T-cell, $CD_4$ and $CD_8$), or splenic B-cell number, or from an increased number of thymocytes. Other cells involved in the immune system response include natural killer cells, macrophages, and neutrophils. In addition, the stimulation may be due to an increase in antibody production in response to an immunogen.

As used herein, the expressions "compromised immune system" and "condition in which insufficient immunoglobulin production occurs" signify the immune system of humans as well as animals that have a smaller antibody response to antigens than normal, whether because their spleen size is smaller than it should be, whether the spleen is only partially functional, whether drugs such as chemotherapeutic agents are suppressing the normal immune function, whether the animal is functionally IGF-I (or GH) deficient, or due to any other factor. Examples include aged patients, patients undergoing chemotherapy or radiation therapy, recovering from a major illness, or about to undergo surgery, patients with AIDS, patients with congenital and acquired B-cell deficiencies such as hypogammaglobulinemia, common varied agammaglobulinemia, and selective immunoglobulin deficiencies, e.g., IgA deficiency, patients infected with a virus such as rabies with an incubation time shorter than the immune response of the patient, and patients with hereditary disorders such as diGeorge syndrome. The mammals and avians potentially affected herein include mammals and avians of economic importance such as bovine, ovine, and porcine animals, as well as chickens and turkeys. The mammals may exhibit a splenic atrophy and subsequent loss in B-cell number and function The preferred mammal herein is a human.

As used herein, "IGF-I" refers to insulin-like growth factor from any species, including bovine, ovine, porcine, equine, avian, and preferably human, in native-sequence or in variant form, and from any source, whether natural, synthetic, or recombinant. Preferred herein for animal use is that form of IGF-I from the particular species being treated, such as porcine IGF-I to treat pigs, ovine IGF-I to treat sheep, bovine IGF-I to treat cattle, etc. Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations. Also preferred for use is IGF-I that has a specific activity greater than about 14,000 units/mg as determined by radioreceptor assay using placenta membranes, such as that available from KabiGen AB, Stockholm, Sweden.

The most preferred IGF-I variants are those described in PCT WO 87/01038 published Feb. 26, 1987 and in pCT WO 89/05822 published June 29, 1989, i.e., those wherein at least the glutamic acid residue is absent at position 3 from the N-terminus of the mature molecule or those having a deletion of up to five aming acids at the N-terminus. The most preferred variant has the first three aming acids from the N-terminus deleted (variously designated as brain IGF, tIGF-I, des(1-3)-IGF-I, or des-IGF-I).

As used herein, "GH" refers to growth hormone from any species, including bovine, ovine, porcine, equine, avian, and preferably human (hGH), in native-sequence or in variant form, and from any source, whether natural, synthetic, or recombinant. This includes both Met-hGH [U.S. Pat. No. 4,755,465 issued Jul. 5, 1988 and Goeddel et al., Nature. 282:544 (1979)], which is sold under the trademark PROTROPIN ® by Genentech, Inc. and is identical to the natural polypeptide, with the exception of the presence of an N-terminal methionine residue, and recombinant hGH (rhGH), available to clinical and research investigators from Genentech, Inc. under the trademark Nutropin ®, and commercially available from Eli Lilly, that lacks this methionine residue and has an aming acid sequence identical to that of the natural hormone. See Gray et al., Biotechnology, 2:161 (1984). Both met-hGH and rhGH have equivalent potencies and pharmacokinetic values. Moore et al., supra. Another suitable hGH candidate is an hGH variant that is a placental form of GH with pure somatogenic and no lactogenic activity. U.S. Pat. No. 4,670,393 issued 2 June 1987.

As used herein, the expression "increasing antibody response to an immunogen" refers to raising the serum immunoglobulin (IgG) titer of an animal in response to a boost of the antigen against which the IgG is directed. Indicators of increased antibody response include an increase in the production of antibodies to booster shots of immunogen, as well as an increase in the number of B-cells in the patient. The immunogen can be any that raise antibodies directed thereto, but preferably is a virus, including a vaccine, or a bacterium. The invention is particularly useful for those instances where the mammal or avian is infected with a virus that has an incubation time that is shorter than the immune response of the mammal or avian, such as, e.g., rabies. The IGF-I herein decreases the interval between primary and secondary immunizations or between secondary immunization and subsequent boosts of immunogen.

As used herein, the expression "increasing the T-cell responsiveness to an immunogen" in a subject suffering from a condition in which insufficient T-help or T-cytolytic activity occurs refers to raising the level of T-helper and/or T-cytolytic cell activity of the mammal in response to an immunogen to which T-cells are responsive, including viral antigens, tumors, bacteria, etc. A subject with insufficient T-help or T-cytolytic activity is a mammal that has less than the normal number of T-helper and/or T-cytolytic cells (as determined, e.g., by $CD_4/CD_8$ markers) necessary to, for example, secrete antibodies, activate macrophages, and kill target cells such as virally infected or tumor cells.

As used herein, the expression "restore immunity" in a mammal means to bring the level of immunity of the mammal back to normal, whether by restoring splenic or thymic cells or by increasing T-cell responsiveness or the amount of immunoglobulin produced by B-cells.

B. Modes for Carrying Out the Invention

For the various purposes of this invention, the IGF-I is directly administered to the mammal or avian by any suitable technique, including parenterally, and can be administered locally or systemically. The specific route of administration will depend, e.g., on the medical history of the patient, including any perceived or anticipated side effects using IGF-I. Examples of parenteral administration include subcutaneous, intramuscular, intravenous, intraarterial, and intraperitoneal administration.

Most preferably, the administration is by continuous infusion (using, e.g., minipumps such as osmotic pumps), or by injection using, e.g., intravenous or subcutaneous means. Preferably, the administration is subcutaneous for IGF-I. The administration may also be as a single bolus or by slow-release depot formulation. Most preferably, the IGF-I is administered continuously by infusion, most preferably subcutaneously.

In addition, the IGF-I is suitably administered together with any one or more of its binding proteins, for example, IGFBP-2, IGF-BP-4, or, most preferably, IGFBP-3, which is described in WO 89/09268 published Oct. 5, 1989 and by Martin and Baxter, J. Biol. Chem., 261:8754–8760 (1986). This glycosylated protein is an acid-stable component of about 53 Kd on a non-reducing SDS-PAGE gel of a 125–150 Kd glycoprotein complex found in human plasma that carries most of the endogenous IGFs and is also regulated by GH. The IGF-I is also suitably coupled to a receptor or antibody or antibody fragment for administration.

The IGF-I composition to be used in the therapy will be formulated and dosed in a fashion consistent with good medical practice, taking into account the clinical condition of the individual patient (especially the side effects of treatment with IGF-I alone), the site of delivery of the IGF-I composition, the method of administration, the scheduling of administration, and other factors known to practitioners. The "effective amount" of IGF-I for purposes herein (including an immune-stimulating effective amount) is thus determined by such considerations.

As a general proposition, the total pharmaceutically effective amount of the IGF-I administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the IGF-I is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The key factor in selecting an appropriate dose is the result obtained, as measured by increases in antibody production, increases in splenocyte or thymocyte number, increases in splenic B-cells, etc.

A course of IGF-I treatment to affect the immune system appears to be optimal if continued longer than a certain minimum number of days, 7 days in the case of the mice. The length of treatment needed to observe changes and the interval following treatment for responses to occur appear to vary depending on the desired effect.

The IGF-I is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (U. Sidman et al., *Biopolymers*, 547-556 (1983)), poly(2-hydroxyethyl methacrylate) (R. Langer et al., *J. Biomed. Mater. Res.*, 15:167-277 (1981), and R. Langer, *Chem. Tech.*, 12:98-105 (1982)), ethylene vinyl acetate (R. Langer et al., id.) or poly-D-(-)-3-hydroxybutyric acid (EP 133,988). Sustained-release IGF-I compositions also include liposomally entrapped IGF-I. Liposomes containing IGF-I are prepared by methods known per se: DE 3,218,121; Epstein et al., *Proc. Natl. Acad. Sci. U.S.A.*, 82:3688-3692 (1985); Hwang et al., *Proc. Natl. Acad. Sci. U.S.A.*, 77:4030-4034 (1980); EP 52,322; EP 36,676; EP 88,046; Ep 143,949; Ep 142,641; Japanese Pat. Appln. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal IGF-I therapy.

For parenteral administration, in one embodiment, the IGF-I is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I uniformly intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The IGF-I is typically formulated in such vehicles at a concentration of about 0.1 mg/ml to 100 mg/ml, preferably 1-10 mg/ml, at a pH of about 3 to 8. Full-length IGF-I is generally stable at a pH of no more than about 6; des(1-3)-IGF-I is stable at about 3.2 to 5. It will be understood that use of certain of the foregoing excipients, carriers, or stabilizers will result in the formation of IGF-I salts.

In addition, the IGF-I, preferably the full-length IGF-I, is suitably formulated in a suitable carrier vehicle to form a pharmaceutical composition that does not contain cells. In one embodiment, the buffer used for formulation will depend on whether the composition will be employed immediately upon mixing or stored for later use. If employed immediately, the full-length IGF-I can be formulated in mannitol, glycine, and phosphate, pH 7.4. If this mixture is to be stored, it is formulated in a buffer at a pH of about 6, such as citrate, with a surfactant that increases the solubility of the GH at this pH, such as 0.1% polysorbate 20 or poloxamer 188. The final preparation may be a stable liquid or lyophilized solid.

IGF-I to be used for therapeutic administration must be sterile. Sterility is readily accomplished by filtration through sterile filtration membranes (e.g., 0.2 micron membranes).

Therapeutic IGF-I compositions generally are placed into a container having a sterile access port, for example, an intravenous solution bag or vial having a stopper pierceable by a hypodermic injection needle.

IGF-I ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous lGF-1 solution, and the resulting mixture is lyophilized. The infusion solution is prepared by reconstituting the lyophilized IGF-I using bacteriostatic Water-for-Injection.

Also, GH may be combined with the IGF-I for this purpose, in a dose and using a suitable administration as is used for IGF-I above. It is noted that hGH is stable at a higher pH than IGF-I, e.g., 7.4–7.8. When GH is administered, it is suitably administered together with one or more of its binding proteins. A well characterized such binding protein is the high-affinity growth hormone binding protein (GHBP) constituting the extracellular domain of the GH receptor that circulates in blood and functions as a GHBP in several species [Ymer and Herington, *Mol. Cell. Endocrino.*, 41:153 (1985); Smith and Talamantes, *Endocrinology*, 123:1489–1494 (1988); Emtner and Roos, *Acta Endocringlogica (Copenh.)*, 122:296–302 (1990)], including man. Baumann et al., *J. Clin. Endocringl. Metab.*, 62:134–141 (1986); EP 366,710 published May 9, 1990; Herington et al., *J. Clin Invest.*, 77:1817–1823 (1986); Leung et al., *Nature*, 330:537–543 (1987). A second BP with lower affinity for GH has also been described that appears to be structurally unrelated to the GH receptor. Baumann and Shaw, *J. Clin. Endocringl. Metab.*, 70:680–686 (1990).

The doses of both GH and IGF-I can be less if used together than if IGF-I is administered alone. It is noted that practitioners devising doses of both IGF-I and GH should take into account the known side effects of treatment with these hormones. For hGH the side effects include sodium retention and expansion of extracellular volume [Ikkos et al., *Acta Endocringl.* (Copenhagen), 32:341–361 (1959); Biglieri et al., *J. Clin. Endocrinol. Metab.*, 21:361–370 (1961)], as well as hyperinsulinemia and hyperglycemia. The major apparent side effect of IGF-I is hypoglycemia. Guler et al., *Proc. Natl. Acad. Sci. USA.* 1989, supra.

Preferably, the IGF-I is administered in conjunction with (i.e., at the same time as or after) a vaccine, such as an AIDS vaccine (for example, a gp120 or gp160 vaccine or a cocktail of gp receptor-based vaccines), either during initial immunization or during a boost of the vaccine, to ensure increased antibody response. Most preferably, the IGF-I is given at the time of each boost. The use of IGF-I with vaccine will increase the effectiveness of the vaccine, particularly in those patients who have compromised immune systems.

It is another embodiment of this invention to diagnose immune-deficient mammals to determine if they have low serum IGF-I levels that could cause their malady and that could be reversed by treatment with IGF-I. Such human patients might include those who are aged, underfed, malnourished, or ill. Diagnosing the serum IGF-I level of such immune-deficient patients and restoring IGF-I blood concentrations in those patients with lower-than-normal serum IGF-I levels by administering an amount of IGF-I effective for that purpose would restore immunity in the patient.

Diagnosing IGF-I levels in a patient can be accomplished by any standard technique, but is typically done by subjecting a blood sample to an ELISA or RIA test using anti-IGF-I antibodies such as described in Furlanetto et al., *J. Clin. Invest.*, 60:648–657 (1977); Bala and Bhaumick, *J. Clin. Endocrin. and Metabol.*, 49:770–777 (1979); and Zapf et al., *J. Clin. Invest.*, 68:1321–1330 (1981).

The invention will be more fully understood by reference to the following examples. They should not, however, be construed as limiting the scope of the invention.

All literature and patent citations are expressly incorporated by reference.

EXAMPLE I

Evaluation of Organ Weights, B- and T-Cell Numbers, And Response to Mitogenic Stimulation Recombinant human IGF-I [available commercially from KabiGen AB, Stockholm, Sweden (specific activity > 14,000 U/mg by radioreceptor assay using placental membranes) or available for clinical investigations from Genentech, Inc., South San Francisco] was employed in all the IGF-I experiments detailed in the examples. The IGF-I was dissolved at 5 mg/ml in 10 mM citrate buffer and 126 mM NaCl, pH 6.0.

This IGF-I was administered to three species, i.e., rat, rabbit, and mouse, to observe its effects on spleen and thymus weight. Dose-response studies were performed in the mouse and rat, and IGF-I was given to the rabbit with similar effects. In addition, B- and T-cell numbers and responses to mitogenic stimulation were evaluated in the mice.

I. Rats

Two animal models of GH deficiency and therefore IGF-I deficiency were used to demonstrate the effect of IGF-I on spleen and thymic weight and size. A third model of GH and IGF-I deficiency is the aged animal. Aged (18-month-old) rats were used to demonstrate the effect of IGF-I on spleen and thymic size, cellulants architecture, and in vitro response to mitogens. Also, adult ovariectomized rats, with normal serum IGF-I concentrations, were used to demonstrate the effect of IGF-I on spleen and thymus in an animal that was not IGF-I deficient.

A. Dwarf Rats

Female dwarf rats (Simonsen Labs, Gilroy, CA) (100–140 g) were dosed by subcutaneous (sc) infusion from osmotic mini-pumps for one week with IGF-I. FIG. 1 provides a dose-response graph for IGF-I on spleen size in these dwarf rats. Clearly, IGF-I is a very potent stimulant to splenic growth in the dwarf rat.

B. Hypophysectomized Rats

Figure 2A:
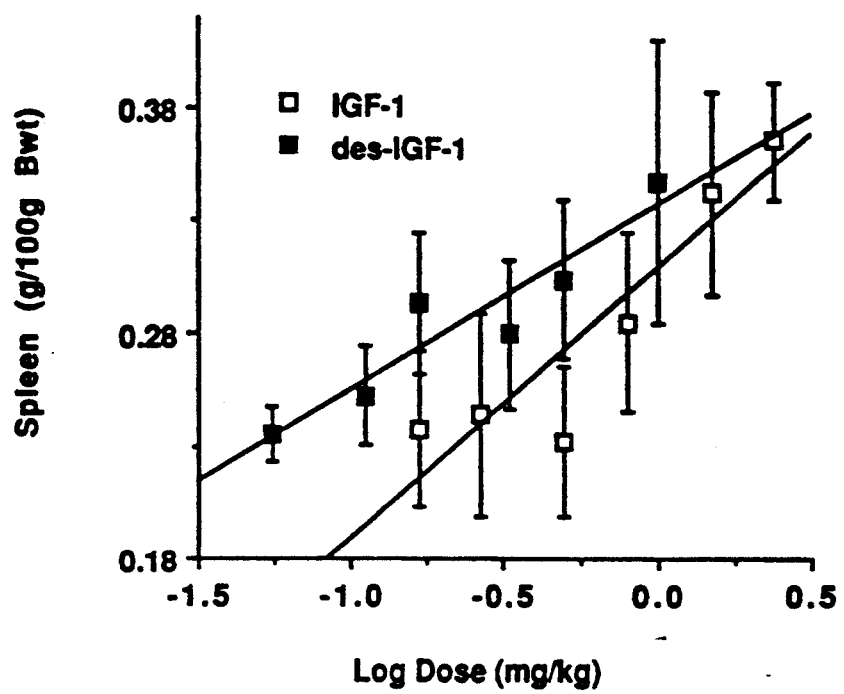
FIGS. 2A and 2B represent graphs of the spleen-to-body weight ratio and thymus-to-body weight ratio, respectively, in hypophysectomized rats treated with IGF-I or des-IGF-I by minipump for 7 days.
Figure 2B:
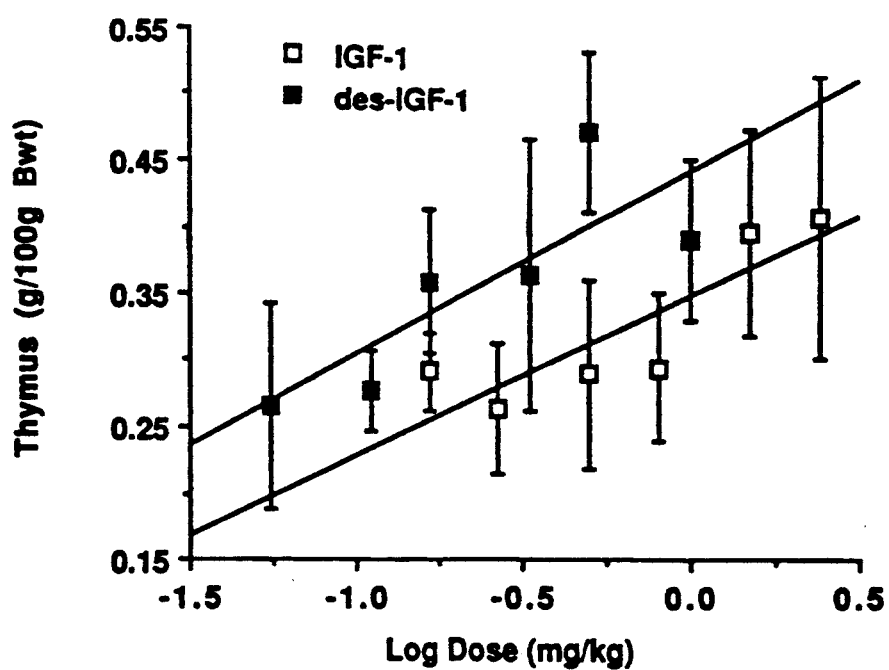

Female hypophysectomized rats (Taconic Farms, Germantown, NY), weighing 85–105 g, were implanted sc with osmotic mini-pumps that delivered IGF-I and des-IGF-I [PCT WO 87/01038 published Feb. 26, 1987 and in pCT WO 89/05822 published Jun. 29, 1989] over one week. The treatment with IGF-I and des-IGF-I shows a greatly enhanced growth response of the spleen and the thymus, as indicated in FIGS. 2A and 2B, respectively. This growth is greater than that of the whole body, as when the weight of the spleen or thymus is expressed per gram of body weight, there is still a very significant growth of the spleen and thymus. Both IGF-I and des-IGF-I have this activity, with des-IGF-I being significantly more potent than IGF-1 in this regard.

C. Adult Female Rats

Adult female rats were ovariectomized. Thirty days later when the rats weighed 300 g they were implanted with osmotic minipumps (Alza, Palo Alto, 2ML2) containing IGF-I (delivering 1.33 or 4 mg/kg/day of IGF-I) or excipient. At sacrifice 14 days after minipump implantation, the spleens were dissected and weighed (the thymus was not dissected in this experiment).

Figure 3:
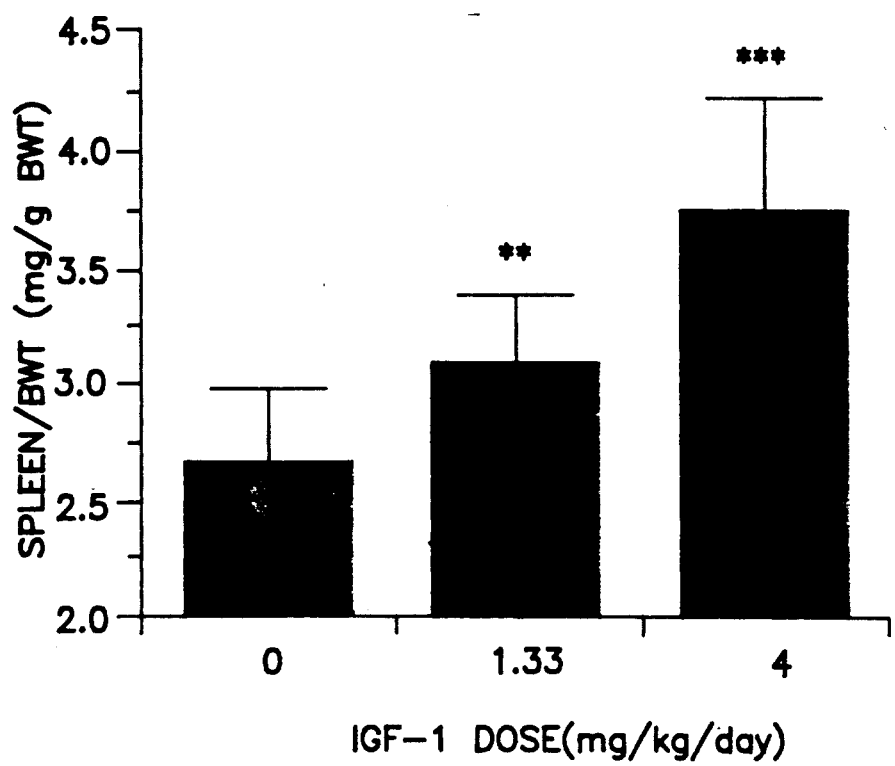
FIG. 3 represents a graph of the spleen-to-body weight ratio of adult female rats treated with IGF-I for 14 days.

FIG. 3 shows the dose-response graph for IGF-I in this rat model. It can be seen that even in a pituitary intact animal with normal endogenous growth hormone and IGF-I it was possible to demonstrate a large effect of exogenous IGF-I on body weight (an average gain of 45 g) and spleen weight. Even when the spleen weight was expressed as a percentage of body weight, very significant growth of the spleen could be demonstrated (*$p<0.001$ vs. excipient, $p<0.01$ vs. excipient).

Therefore, in the rat, IGF-I could be seen to affect the growth of tissues with immune functions in GH- and IGF-I-deficient animals (immune-deficient animals) and in animals with normal GH and IGF-I concentrations (immune-competent animals).

D. Aged Rats

In two separate in vivo studies, IGF-I, GH, or IGF-I plus GH were administered for 14 days to aged 18-month-old rats to determine whether IGF-I could induce functional changes in spleen and thymus in this model of thymic regression.

(i) Design

Male Fischer 344 rats of 18 months of age and 400–500 g were purchased from Harlan Sprague Dawley (HSD). These rats were bred by HSD for the NIH Institute for Aging and are the standard rat model used in aging studies. In Experiment One, 7 rats/group were employed, and in Experiment Two, 8 rats/group. Young F344 rats (5–8 weeks old), which were housed identically as experimental rats, were used as positive controls. The treatment groups were: (1) excipient pumps, excipient injections, (2) IGF-I pumps, excipient injections, (3) IGF-I pumps, GH injections, (4) excipient pumps, GH injections, and (5) young rats.

The IGF-I was loaded into two minipumps so that 1.150 mg/rat/day of IGF-I or 0.8 mg/kg/day of des-IGF-I was delivered sc as a continuous infusion. The rhGH (Nutropin ® brand, Genentech, Inc. formulated at 2 mg/ml in 18 mg/ml mannitol, 0.68 mg/ml glycine, and 5 mM phosphate, pH 7.4) or bGH (Monsanto) was given as a daily sc injection of 1 mg/rat/day. The excipient pump groups received identical pumps filled with the excipient for IGF-I (10 mM citrate buffer and 126 mM NaCl, pH 6.0), hereinafter called "IGF-I excipient." The treatments continued for 14 days. The animals no receiving GH were injected (0.1 ml) with hGH vehicle each day.

At sacrifice, a blood sample was taken, and the liver, kidneys, heart, spleen, and thymus were removed, blotted dry, and immediately weighed. The spleen and thymus were immediately placed in buffer and then cells were obtained by digestion or physical rupture. The cells were counted and then plated out at uniform density. The thymic cells were cultured with IL-1 (2 U/ml) and phytohemaglutinin (PHA) (5 μg/ml) and thymidine incorporation was measured as described by Maizel et al., *J. Exp. Med.*, 153:470–476 (1981). The spleens were similarly treated and two tests of function were performed.

(ii) Results (a) Experiment One

Figure 4:
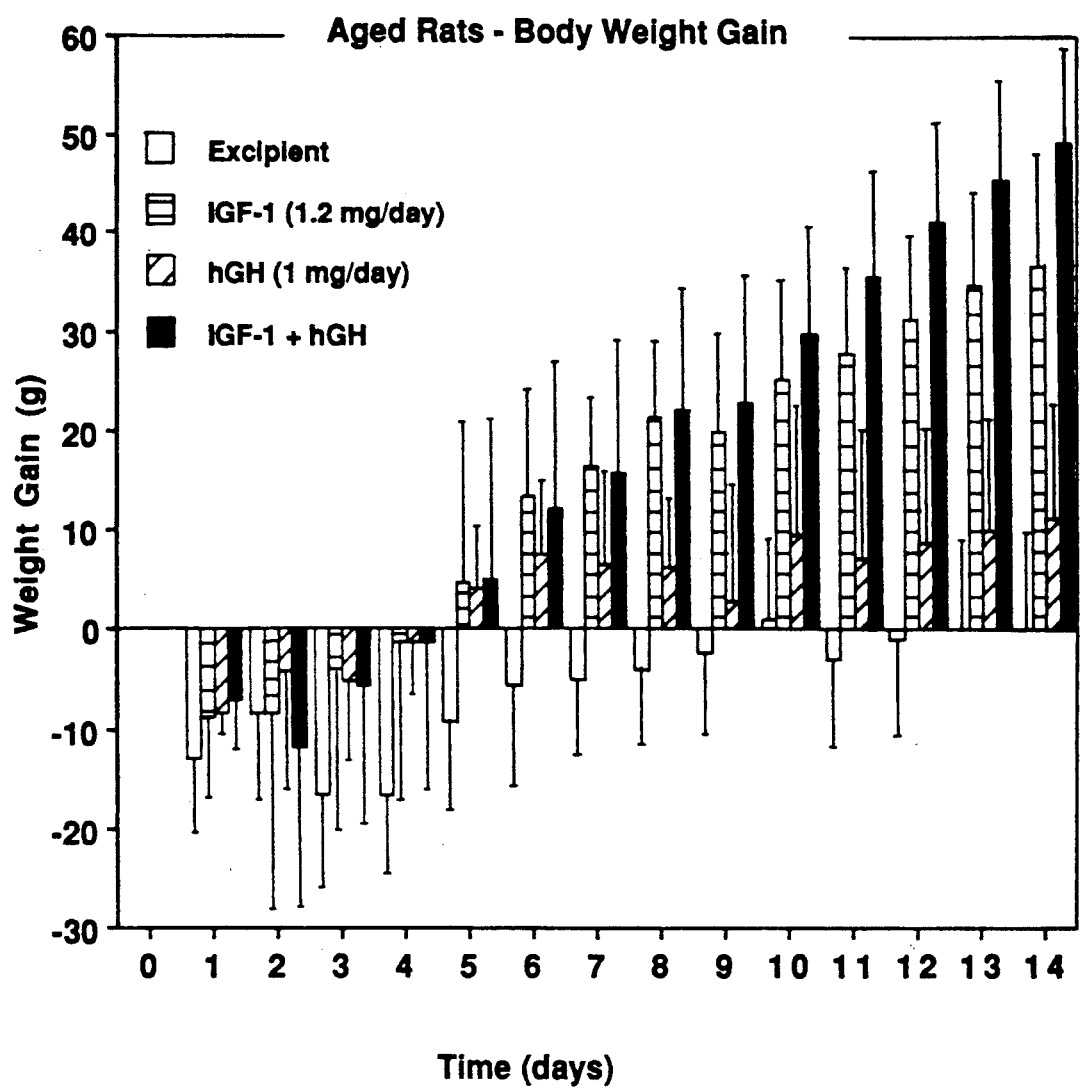
FIG. 4 is a graph of body weight gain in aged rats treated with excipient, IGF-I, hGH, or IGF-I plus hGH.

Full-length IGF-I and rhGH were employed in this experiment. FIG. 4 shows the body weight gain. After 14 days control rats had not gained weight. GH-treated rats gained 9.6±11.4 g, IGF-I-treated rats gained 34.5±9.4 g, and IGF-I- and GH-treated rats gained 45.5±9.9 g. The response to IGF-I was clearly large, and the response to GH plus IGF-I appeared to be additive. IGF-I at the doses used was markedly anabolic. A very dramatic effect of IGF-I treatment was the large fall in blood urea nitrogen (BUN) levels from 20.7±2.4 mg/dL in controls to 13.8±1.8 mg/dL after IGF-I treatment; hGH had no effect. A lowered BUN indicates an anabolic metabolic state. The body weight gain data, the increased organ weights, the lowered BUN, and the lowered blood enzyme levels all indicate that IGF-I was producing an anabolic state where protein synthesis was predominant over protein breakdown. The effect of IGF-I was clearly greater than that of hGH.

There was a clear effect of IGF-I on all the organ weights. Liver increased by 6.6%, kidneys by 16.6%, heart by 18.5%, thymus by 27.0%, and spleen by 80.8%. All the responses were statistically significant. The only effect of hGH was to reduce liver weight significantly by 8.8%. Combined GH and IGF-I treatment did not reduce the magnitude of the effect of IGF-I on these organs, with one exception. Spleen weight was reduced for the IGF-I plus GH treatment compared to the weight of the spleen in the IGF-I alone group.

Total IGF-I levels were increased by IGF-I administration with or without concurrent hGH treatment. By itself, hGH did not significantly elevate blood total IGF-I levels.

The cells from the harvested organs were dispersed and their response to mitogens was measured. Table I shows some of the data for the thymus and spleen. The wet weight of the thymus was increased by IGF-I but not by hGH. Normal, young, 60-day-old Fischer rats were run as positive controls.

TABLE I

Cell Number in Spleen ($\times 10^8$) and Thymus ($\times 10^7$)

| Group | No. Spleen Cells | No. Thymic Cells |
|---|---|---|
| Young Rats | 2.81 ± 0.30 | 4.43 ± 0.79*** |
| Old Rats Excipient | 2.72 ± 0.68 | 0.19 ± 0.15 |
| Old Rats IGF-1 | 3.58 ± 0.86 | 0.96 ± 0.66** |
| Old Rats IGF-1 + GH | 3.27 ± 1.47 | 0.82 ± 0.27*** |
| Old Rats GH | 2.50 ± 0.51 | 0.36 ± 0.28* |

Values are Means and Standard deviations.
(Significances: *$p < 0.05$, $p < 0.01$, *$p < 0.001$ vs Excipient)

None of the thymi from the untreated old rats yielded sufficient cells to allow full analysis in tissue culture. In contrast, 8 of the 13 rats treated with IGF-I or IGF-I plus GH did yield sufficient viable thymic cells. IGF-I treatment for 14 days caused a remarkable 5-fold increase in the number of thymic cells, although the thymus of the younger rats still contained substantially more cells.

Growth hormone tended to increase the number of thymic cells, but the effect (a doubling of the mean number) was not statistically significant. IGF-I plus hGH was also an effective way to increase thymic cell number. In contrast, the number of cells in the spleen was not significantly increased by IGF-I or GH treatment, although the mean values of the IGF-I-treated groups were higher. Therefore, IGF-I could increase the wet weight of the thymus and also the number of cells capable of being harvested. Then, any functional effect of the increased tissue mass and cell number was tested in vitro by measuring the responses of the dispersed thymocytes to mitogens, as shown in Table II below.

For both the PHA and IL-1 responses and their combination, the tissue from the old rats showed a tendency toward increased activity with IGF-I alone compared to that from the younger animals, although this effect was not statistically significant. There was no additive effect of the IGF-I plus GH combination on the number of cells harvested. It was therefore surprising that IGF-I plus GH had the largest and most significant effect on all measures of thymic function. Compared to the responses of the younger tissue, the PHA response for IGF-I plus GH was increased 3.7-fold and for the PHA plus IL-1 combination the response was increased 4-fold.

These data show that an increased mass of thymic tissue can be produced in an aged animal using IGF-I, and after the relatively short period of only 14 days of IGF-I treatment. There are previous studies in similarly aged rats that show that both GH and prolactin can increase the size and some aspects of thymic function. Kelley, in *Psychoneuroimmunology II*, 2nd Ed., B. Ader et al., eds, 1990, supra.

It has also now been shown that the increased thymic tissue produced by IGF-I is functional tissue, in that it can respond to mitogens. There were four times as many thymic cells in the young rats, but the cells from IGF-I-treated old rats had an in vitro activity that was improved up to 4-fold. Therefore, according to the functional tests used, the thymus of the older rats was essentially restored to that of a much younger animal. In the thymus the effect of aging appeared to have been reversed.

(b) Experiment Two

In a second set of 18-month-old rats, a similar experiment was performed, except that bGH and des-IGF-I were employed. Also tested was the activity of des-IGF-I and whether the relatively poor effect of hGH in the first study was due to hGH antibodies (GH is very antigenic in the rat, bGH much less so).

The results are shown in Table III. The weight gains with des-IGF-I seemed less than in the first study, but were still superior to the response to bGH. The kidney and spleen showed large responses to des-IGF-I, and no significant response to GH. In general, des-IGF-I returned the blood cell counts toward those in the younger animals, with the combination of des-IGF-I and bGH being the most affective treatment. des-IGF-I tended to increase the white blood cell (WBC) and the lymphocyte number when combined with bGH. This change is similar in amount to that seen in Example IV, in man.

The results of thymic weight, cell number, and percentage of cells that were PNA (peanut agglutinin) positive are shown in Table IV. It can be seen that thymus weight was increased at sacrifice in the des-IGF-I-treated rats. This experiment was designed to test the origin and type of increased cell number in the thymus. This discrimination of the origin and type of cells was achieved by FACS analysis (described further below) using PNA as the specific marker for true thymocytes. PNA positive thymocytes are believed to be young precursor cells for T-cells.

TABLE II

Thymic cells from young and old F344 rats. Untreated old rats all had insufficient thymic cells to run the assays.

| Treatment | Cell No. | PHA | IL-1 | PHA + IL-1 |
|---|---|---|---|---|
| Young Rat | 4.96 | 1764 | 1360 | 3349 |
| Young Rat | 4.80 | 1790 | 989 | 3836 |
| Young Rat | 3.52 | 2112 | 1462 | 3629 |
| Mean | | 1888 ± 193 | 1270 ± 249 | 3604 ± 244 |
| Old Rats | | | | |
| IGF-1 | 0.37 | 3078 | 672 | 11273 |
| IGF-1 | 1.72 | 3524 | 1028 | 3724 |
| IGF-1 | 1.68 | 3032 | 854 | 6532 |
| IGF-1 | 1.20 | 1523 | 929 | — |
| Mean | | 2789 ± 872* | 870 ± 150** | 7176 ± 3815* |
| Old Rats | | | | |
| IGF-1 + GH | 0.92 | 10436 | 1536 | 18990 |
| IGF-1 + GH | 1.06 | 5120 | 2836 | 17446 |
| IGF-1 + GH | 1.12 | 7432 | 2316 | 13429 |
| IGF-1 + GH | 0.78 | 5095 | 1796 | 7865 |
| Mean | | 7020 ± 2526## | 2121 ± 576# | 14432 + 4966## |
| Old Rats | | | | |
| GH | 0.72 | 2005 | 581 | 4371 |
| GH | 0.82 | 11263 | 1780 | 27021 |
| Mean | | — | — | — |

Values are mean c.p.m. from individual animals, the group means are based on these values
Comparisons (#IGF-1 + GH vs Young; *IGF-1 vs IGF-1 + GH)
(Significances: *p < 0.05, **p < 0.01, #p < 0.05, ##p < 0.01)

TABLE III

Blood Counts: Aged rats treated with des-IGF-1 and GH; cf. Young Rats

| Group | WBC | Lympcte No | Hematocrit | RBC no | MCV | Platelet No. |
|---|---|---|---|---|---|---|
| a Control Old | 7.36 ± 1.42 | 4.32 ± 0.75 | 38.0 ± 1.8 | 7.59 ± 0.49 | 50.1 ± 1.1 | 676 ± 29 |
| b des-IGF-1 | 8.12 ± 0.76 | 4.23 ± 0.41 | 37.8 ± 1.8 | 7.29 ± 0.38 | 51.8 ± 0.5 | 726 ± 69 |
| c bGH | 6.97 ± 0.96 | 4.15 ± 0.76 | 37.4 ± 1.3 | 7.39 ± 0.32 | 50.6 ± 0.5 | 795 ± 46 |
| d des + bGH | 8.93 ± 1.90 | 4.80 ± 1.16 | 37.6 ± 1.2 | 7.01 ± 0.22 | 53.9 ± 1.6 | 783 ± 98 |
| e Young Rats | 8.92 ± 1.24 | 6.40 ± 0.81 | 37.5 ± 0.9 | 6.53 ± 0.14 | 57.4 ± 1.0 | 897 ± 68 |

Means and Standard Deviations n = 7 & 8, except for group (e) where (n = 4).

TABLE IV

Thymus Cell Counts: Aged F344 rats treated with des-IFG-1 and bGH; cf. Young Rats

| Group | Thymus Wt (mg) | Cell No. (×10⁶) | PNA+ (%) |
|---|---|---|---|
| a Excipient Old | 80 ± 35 | 0.66 ± 0.2 | 24 ± 12 |
| b des-IGF-1 (0.64 | 117 ± 27* | 3.27 ± 2.1** | 72 ± 14*** |
| c bGH (1.0) | 66 ± 17 | 1.30 ± 0.6 | 37 ± 18 |
| d des + bGH | 144 ± 39** | 2.79 ± 1.5** | 69 ± 23*** |

TABLE IV-continued

Thymus Cell Counts: Aged F344 rats treated with des-IFG-1 and bGH; cf. Young Rats

| Group | Thymus Wt (mg) | Cell No. (×10$^6$) | PNA+ (%) |
|---|---|---|---|
| e Young Rats | 338 ± 30*** | 2.85 ± 0.8** | 94 ± 2*** |

Means and Standard Deviations n = 7 & 8, except for group e (n = 4).

The young rats had 5-fold more thymic cells than the old rats. The number of cells in the thymus was increased about 4.5-fold using des-IGF-I alone or in combination with bGH. By itself, bGH increased cell number only two-fold. These responses confirm the observations in Experiment One. The percentage of the cells that were PNA positive was unexpected. The young control rats had 95% PNA positive cells, and the aged rats only 25% positive cells.

Des-IGF-I by itself in these old rats increased the percentage PNA positive cells to 72% of the cells. A similar number (69%) was seen for the des-IGF-I plus bGH group. bGH by itself did not significantly affect the percentage PNA positive cells. This indicates that "real" thymic repopulation was being regenerated in the old animals, composed of precursor cells for T-cells.

Therefore, des-IGF-I produced a very dramatic effect by returning both the number of cells and the percentage that were PNA positive essentially to normal. IGF-I appears to have a marked effect on the rejuvenation of the thymus in an aged rat. At t sacrifice in Experiment Two in the aged rats, half the thymus was placed in 10% formalin and histological sections were prepared. The general morphology of the thymus was assessed by a veterinary pathologist as being characterized by (1) no significant lesions (the young control animals), or (2) involution (normal for the aged animals), or (3) showing evidence of lymphocytic hyperplasia. In addition, the amount of lymphocytic cellularity within the thymus was graded for all the animals, as this seemed to be the cell component that was different between the groups.

Using this scheme characteristic, thymic involution was seen in the excipient and the GH-treated groups. However, there was clear evidence of lymphocytic hyperplasia and the restoration of the thymic architecture in the groups that received des-IGF-I and des-IGF-I plus bGH. The increase in the lymphocytic cellularity in the rats treated with des-IGF-I was easily distinguishable. Scoring the slides for the degree of involution and the amount of lymphocytic hyperplasia confirmed that involution was significantly reversed by des-IGF-I ($p<0.01$, Fisher's test) and that the amount of lymphocytic hyperplasia was greatly increased by des-IGF-I ($p<0.001$). Therefore, histological examination of the thymus confirmed that IGF-I can rejuvenate the thymus of an aged animal, even where thymic involution has already occurred.

II. Rabbits

Male New Zealand White rabbits 2.0-2.5 kg were anesthetized and renal damage was induced by clamping both renal arteries for 120 minutes. At clamping, either one Alzet osmotic pump (Alza Corporation, Palo Alto, CA, Model 2ML-1) containing 2 ml of 3.3 mg des-IGF-I/ml acetic acid (1 00 mM, pH 4.5), or 2 Alzet osmotic pumps containing 2 ml each of 5.0 mg IGF-I/ml (in sodium chloride/sodium acetate buffer, pH 6.0) were placed in the abdominal cavity. The pumps delivered either 0.364 mg of des-IGF-I/kg/day or 1.18 mg IGF-I/kg/day for 7 days. Control animals received excipient-filled pumps. The animals were sacrificed at day 7 and the thymus and spleen were dissected.

After seven-day treatment with IGF-I the average wet weight of the thymus in IGF-I-treated rabbits (n=6) was 4.7±0.44 g, nearly twice as large as those of the control animals (2.7±0.58 g, n=4, p=0.023). When thymus size was expressed as a percentage of rabbit body weight the statistical significance of the effect increased (p=0.014).

After seven-day treatment with des-IGF-I, the average wet weight of the spleen in treated rabbits (n=8, 2.43±0.44 g) was more than twice as large as that of the control rabbits (n=7, 1.17±0.21 g, p=0.028).

III. Mice

The above studies using rats and rabbits established that IGF-I could cause profound changes in the immune system. The mouse was next used as a model system, as in this species immune cell markers and assays are better characterized and were readily available. Furthermore, it was desired to establish in the mouse if the effects on thymus and spleen size, cell number, and in vitro responses to mitogens were translated into a real functionally enhanced activity of the immune system.

Since it was shown that in aged rats IGF-I had remarkable activity in restoring the architecture and cytology of the thymus to that of a young animal and that the cells produced showed enhanced mitogenic response, aged mice were chosen as the model, in this case retired breeder male mice, which are a model of accelerated aging. The effect of IGF-I as an anabolic agent as well as an effector of immune tissue growth and function was studied in the adult aged mice. In addition, the effect of hGH and a combination of IGF-I and hGH on cell number and mitogenic stimulation was evaluated.

A. Design

1. Protocol

The following studies used retired breeder BALB/c mice 9 months old or older and weighing approximately 25 to 35 g (Harlan Sprague Dawley, San Diego, Calif.). Animals were housed in single cages and given food (Purina Rodent Chow 5010, St. Louis, Mo.) and water, ad libitum. All animals were weighed before being grouped into treatment groups (based on their body weight) using a randomization program. Animals were identified with stainless steel ear tags and were acclimated for at least one week.

IGF-I was administered by sc-implanted osmotic minipump (for 7-day studies, Alzet Model 2001, pump rate approximately 1 µl/hr.; for 14-day studies, two Alzet Model 2002 minipumps, pump rate approximately 0.5 µl/hr; Alza, Palo Alto, Calif.). The pumps were loaded with solution per the manufacturer's instructions, and the filled pumps were then incubated in sterile saline overnight in the refrigerator.

The pumps were filled with either the IGF-I excipient or the desired concentration of IGF-I (5 mg/ml formulated as described above), i.e., 7.5, 30, or 120 µg IGF-I/day/7 days for 6 animals per group for the first seven-day treatment study and 120 µg IGF-I/day/7 days for 5 animals per group for the second seven-day treatment study and the 14-day treatment study.

For hGH treatments, rhGH (Nutropin ® brand) was administered by itself in an amount of 9.6, 48, or 240 µg hGH/day/14 days via two Alzet Model 2002 osmotic minipumps (0.5 µl/hr/14 days) implanted sc to 5 animals per group, or by itself via 240 μg hGH for 14 days via sc injection, 5 animals/group.

For combination studies of IGF-I and GH, IGF-I was administered in a dose of 120 μg by two Alzet 2002 minipumps and GH was administered by daily sc 240-μg injections into 5 animals/group.

The mice were anesthetized with an ip injection of approximately 0.4 ml of avertin (2,2,2-tribromoethanol and tert-amyl alcohol in phosphate buffered saline (PBS)). The dorsal scapular region was then clipped of hair and a small incision was made. A close hemostat was then inserted into the incision and pushed posteriorly. A minipump was then inserted into the pocket and the incision was closed with stainless steel wound clips, and a sc injection of 7500 U of penicillin was given. Animals were inspected daily and their body weights recorded.

Animals were sacrificed at various times following minipump placement, a large blood sample was taken, and the thymus, spleen, heart, liver, kidney, and mandibular and mesenteric lymph nodes from each treatment group were removed aseptically and weighed. The spleen, thymus, and lymph nodes were placed on ice in tissue culture media in separate vials for further assays. All data are expressed as the mean±standard deviation, with comparisons being made by one-way analysis of variance with follow-up comparisons being made using Duncan's Range Test.

3. Cell Preparation

The lymph nodes, spleen and thymus were dispersed using sintered glass slides to form single cell suspensions. The cells were then washed, in Eagle's minimal essential medium (MEM, Gibco, Grand Island, N.Y.) containing 10% fetal bovine serum (FBS) (Gibco), penicillin (100 units/ml), 100 μg/ml streptomycin (Gibco), and 200/mM glutamine, and resuspended at $5 \times 10^6$ viable cells/ml as determined by trypan blue dye exclusion.

4. Mitogen Stimulation

Lipopolysaccharide (LPS - E. coli 055:B5) was obtained from Difco Laboratories (Detroit, Michigan). Pokeweed mitogen (PWM) and Concanavalin A (Con A) were obtained from Sigma (St. Louis, Mo.). The response to each mitogen was assayed in triplicate at the following concentrations: LPS (100, 10, 1 μg/ml), PWM (10, 5, 2.5 μg/ml), Con A (10, 5, 2.5 μg/ml). Two hundred microliters of cells ($2.5 \times 10^6$/ml) containing the appropriate dilution of mitogen were cultured in flat-bottom microtiter plates (Falcon Plastics, Oxnard, Calif.) in Hepes (0.5M)-NaHCO:-buffered (0.24% w/v) MEM containing 10% FBS and supplements as described above. Cultures were incubated at 37° C. in 10% $CO_2$.

After 72 hours, the cultures were pulsed with 1 mCi of methyl $^3$H-thymidine. Twelve hours later, the cultures were harvested onto glass fiber filters using a multiple sample harvester. Discs were dried and placed in 3 ml of scintillation fluid. The amount of $^3$H-thymidine incorporated into DNA was measured using a Beckman scintillation counter. Only optimal responses to mitogens, which were the same for all treatment groups, were reported.

5. FACS Analysis

Lymphocyte cell suspensions prepared as described were adjusted to $1 \times 10^6$ cells/ml in PBS containing 0.1% BSA and 10 mM sodium azide. Two-hundred-microliter aliquots of the cell suspensions were incubated for one hour at 4° C. with 5 μl of the appropriate dilution of monoclonal rat anti-mouse FITC conjugate anti-thy-1, anti-L3T4, or anti-Lyt-2 (Caltag, S. San Francisco, Calif.) to stain the T-cell populations. B-cells in these suspensions were stained using FITC-conjugated F(ab')$_2$ polyclonal goat anti-mouse Ig (M,G,A specific) (Becton Dickinson, Mountainview, Calif.). Following three washes with cold medium, cells were analyzed for degree of fluorescence intensity using a FACS 440 (Becton Dickinson, Sunnyvale, Calif.). Fluorescence parameters were collected using a log amplifier after gating on the combination of forward and perpendicular light scatter. Fluorescence data was expressed as percentage of fluorescent cells compared to non-relevant mab of identical isotypes. Fluorescence was measured as mean fluorescence intensity of the fluorescent cells as expressed as mean channel number plotted on a log scale.

B. 7 and 14 Day Studies

The purpose of these studies was to establish if IGF-I was anabolic in the intact normal mouse and if at such anabolic doses IGF-I affected thymic and splenic weight, cellularity, cell type, and responsiveness in vitro to mitogens. Five or six mice per group were used in these studies. On the basis of the doses known to be effective in the rat, it was decided to deliver IGF-I by continuous sc infusion at 140, 46, and 15 μg/mouse/day (approximately 4, 1.33, and 0.44 mg/kg/day).

C. Results

1. Effect of 7-Day Treatment

There was a dose-related effect on body weight gain over the 7 days (excipient 0.75±0.75 g, low dose 0.86±0.63 g, medium dose 1.31±1.03 g, and high dose 3.42±1.24 g), with the high-dose response being highly statistically significant compared to all other groups ($p<0.001$). In the repeat experiment with the high-dose IGF-I a similar weight gain (3.55±0.54 g) occurred that again was statistically greater ($p<0.001$) than the gain of the excipient-treated group.

IGF-I caused significant growth of the spleen and the thymus after 7 days of treatment with IGF-I. In the first experiment there was a clear dose-related effect of IGF-I on the spleen (excipient 105±14, low dose 124±21; medium dose 145±58; high dose 193±23 mg; excipient vs. high-dose IGF-I, $p<0.001$). In the repeat experiment, the spleen weight again increased (excipient 103±18, high dose 206±68 mg, $p=0.01$). Thymus weight was unchanged in the first experiment; this was probably due to the thymus being dissected differently by different dissectors. In the repeat experiment, one dissector uniformly removed the thymus, and significant thymic growth was detected (excipient, 15.2±1.3; high dose 26.2±6.4 mg, $p=0.006$).

Figure 5A:
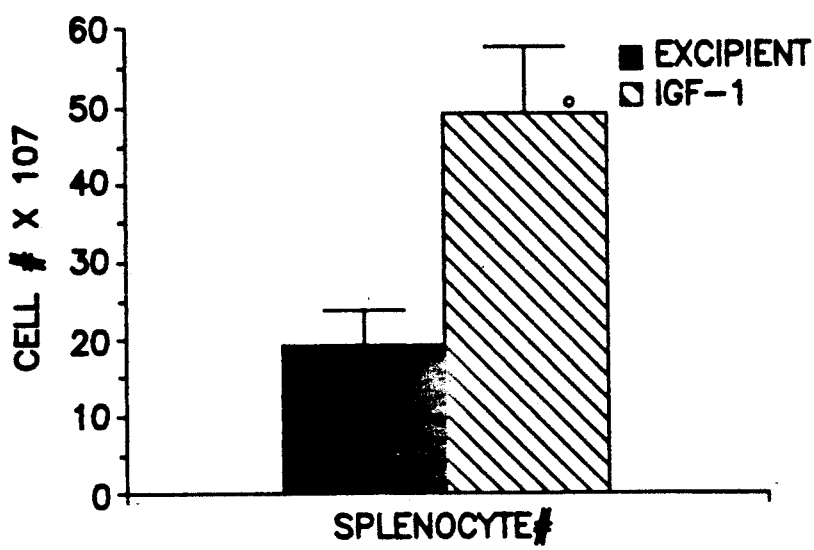
FIGS. 5A, 5B, and 5C provide graphs on the splenocyte number, splenic T-cell population number, and splenic B-cell number, respectively, after 7-day IGF-I treatment or excipient treatment.
Figure 5B:
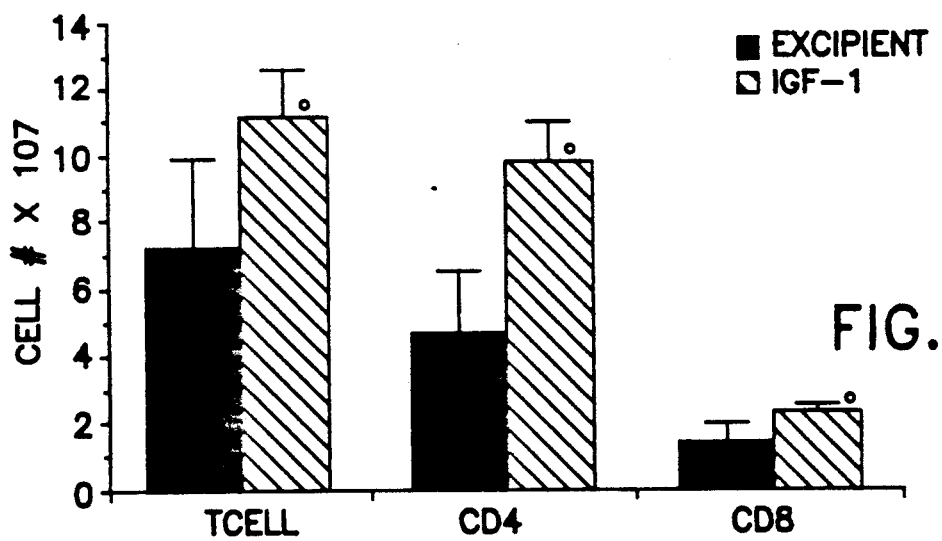
Figure 5C:
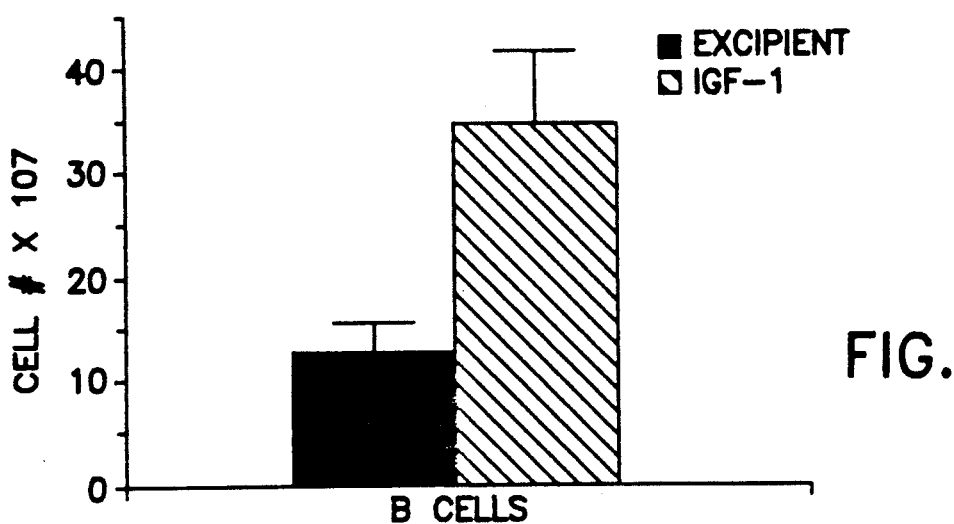

The observed increase in spleen weight following seven-day treatment with 1 40 μg IGF-I/day was due in part to an increase in lymphocyte number. Viable lymphocytes, as determined by trypan blue exclusion, increased from $2 \times 10^8$ to $5 \times 10^8$ cells/spleen following 7-day treatment with IGF-I (FIG. 5). This increase in cell number appeared to be due to an increase in both B- and T-cells. When B- and T-cell numbers were quantitated by FACS analyses of SIg+ and Thy 1+cells, respectively, B-cell number increased 3 fold ($1.3 \times 10^8$ excipient vs. $3.5 \times 10^8$ IGF-I), while T-cell number was also increased compared to controls ($0.7 \times 10^7$ excipients vs. $1.1 \times 10^7$ IGF-I). See FIG. 5.

Figure 6:
FIG. 6 provides a graph on the number of thymocytes after 7-day IGF-I treatment or excipient treatment.

The observed increase in thymic weight correlated with an increase in Thy 1+thymocytes ($1 \times 10^7$ excipient vs. $2.4 \times 10^7$ IGF-I). See FIG. 6. These data suggest that IGF-I has a potent mitogenic effect on lymphocyte subpopulations.

Figure 7A:
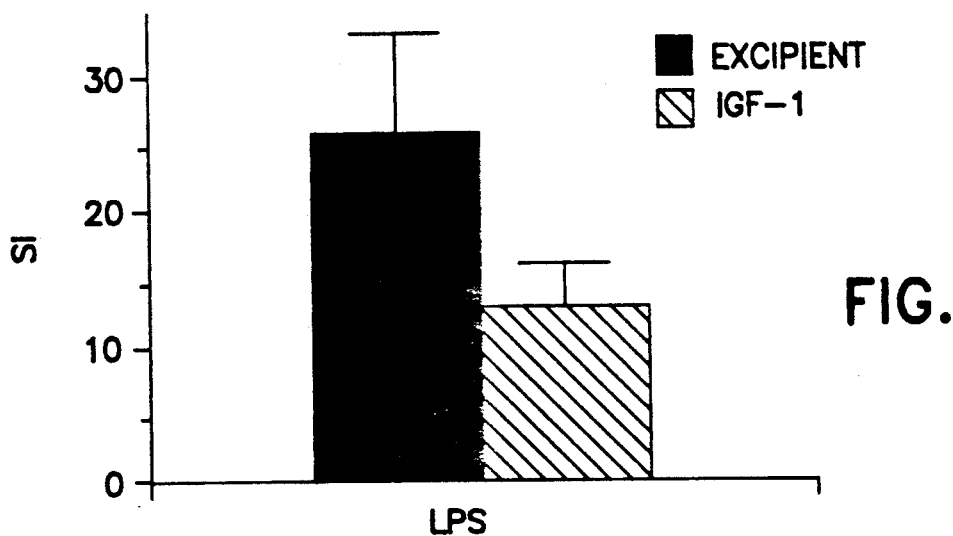
FIG. 7 represents a graph of the mitogenic responses seven days after initial excipient or IGF-I treatment of mice using the mitogens LPS (FIG. 7A), Con A (FIG. 7B), or PWM (FIG. 7C).
Figure 7B:
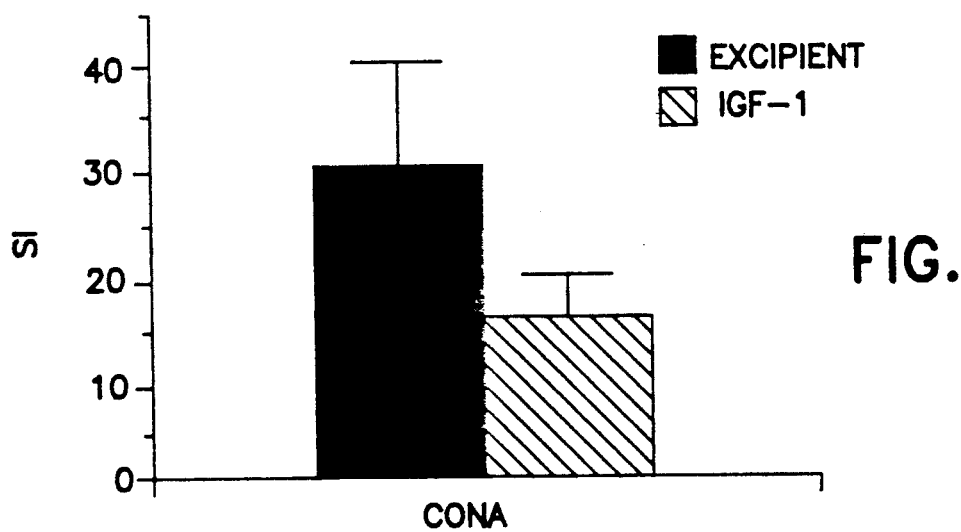
Figure 7C:
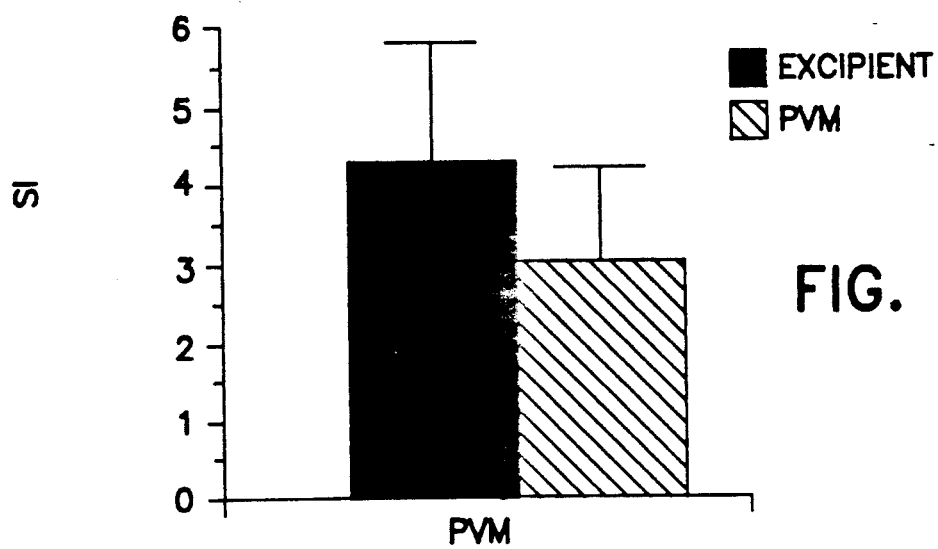

In contrast to the dramatic increase in lymphocyte number induced by IGF-I, the response of splenic lymphocytes to stimulation by LPS (B-cells) and Con A (T-cells) was decreased compared to controls, while the response to PWM was equivalent for both groups of mice. See FIG. 7. This depressed mitogenic response suggests a lack of functional maturity in the lymphocyte population following short-term (7-day) IGF-I treatment.

Therefore, in the 7-day experiment, lymphocyte number was increased, but mitogenic response was depressed.

2. Effect of 14-Day Treatment

Next it was determined if a longer exposure to IGF-I was required to effect lymphocyte function than was required to effect lymphocyte number. Therefore, treatment was extended to 14 days using the high dose of IGF-I (140 μg/mouse/day). Furthermore, since hGH is thought to act in part by inducing IGF-I production, the effects of hGH vs. IGF-I on lymphocyte responses were compared.

There was a significant weight gain after 14 days of treatment with IGF-I (excipient 1.49±0.46; high dose 3.87±0.45 g, p<0.001). Additionally there was significant splenic growth (excipient 96±12; high dose 163±9, p<0.001), and significant thymic growth (excipient 18.2±4.6: high dose 33.8×10.6, p=0.017). It can be seen that the thymus and spleen reached similar weights after 7 or 14 days of treatment.

Figure 8A:
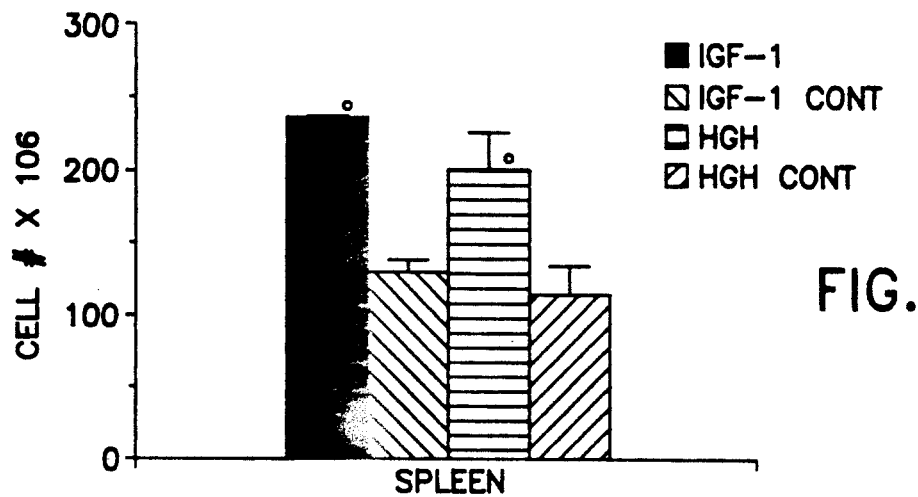
FIGS. 8A, 8B, and 8C provide graphs on the splenocyte number, splenic T-cell population number, and splenic B-cell number, respectively, after 14-day IGF-I treatment or excipient treatment.
Figure 8B:
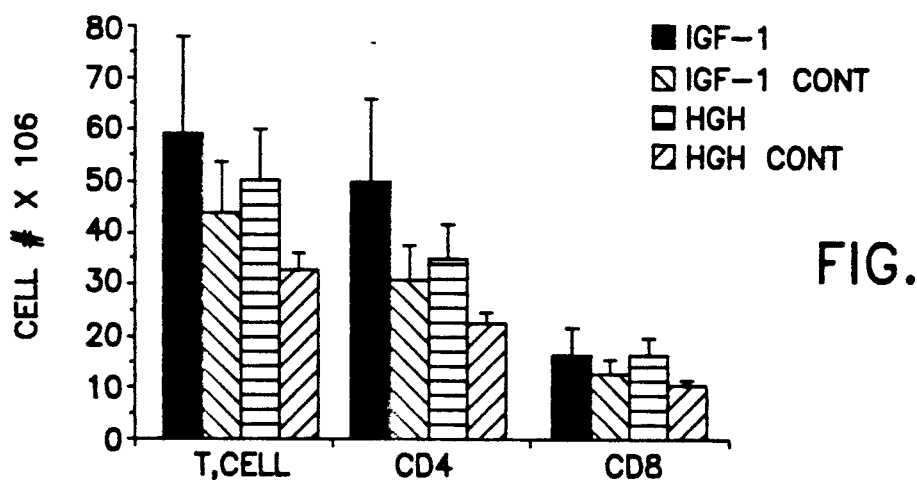
Figure 8C:
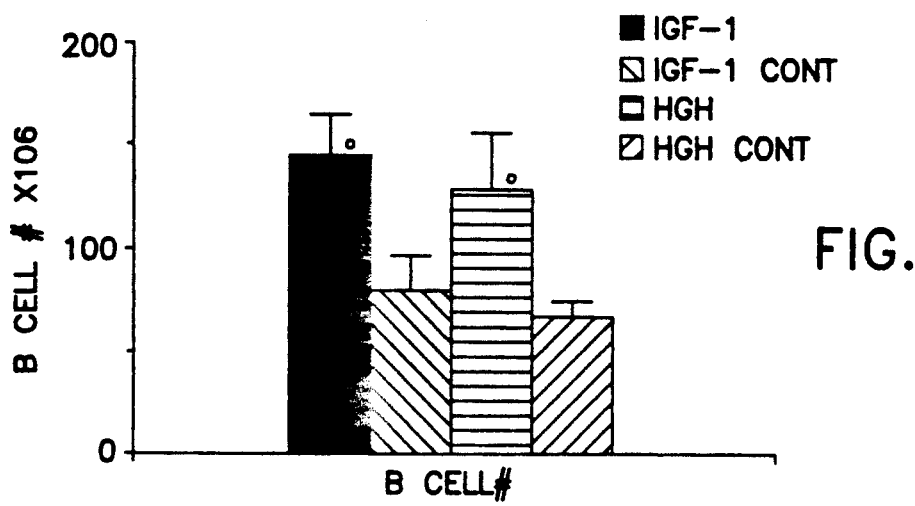
Figure 9:
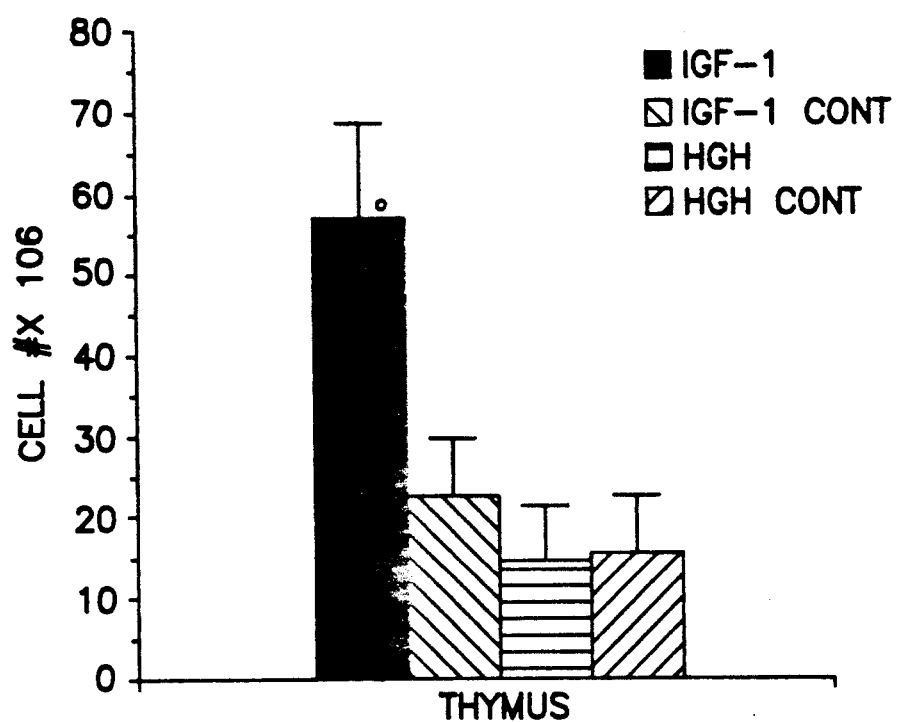
FIG. 9 represents a graph of the number of thymocytes after 14-day IGF-I treatment, hGH treatment, IGF-I control treatment, and hGH control treatment.

As seen in the 7-day experiment, the spleen cell number nearly doubled ($1.3 \times 10^8$ vs. $2.4 \times 10^8$) compared to controls using IGF-I treatment (FIG. 8). While there was an increase in T-cell number in the IGF-I-treated mice, the only statistically significant increase was seen in the CD. population ($3.1 \times 10^7$ vs. $4.9 \times 10^7$) (FIG. 8), suggesting that CD4+cells may be preferentially increased by this treatment regime. As seen in the previous experiment, IGF-I treatment resulted in substantial increases in B-cell number. IGF-I also showed an increase in T-cell number in the thymus when treatment was carried out for 14 days. See FIG. 9.

Figure 10A:
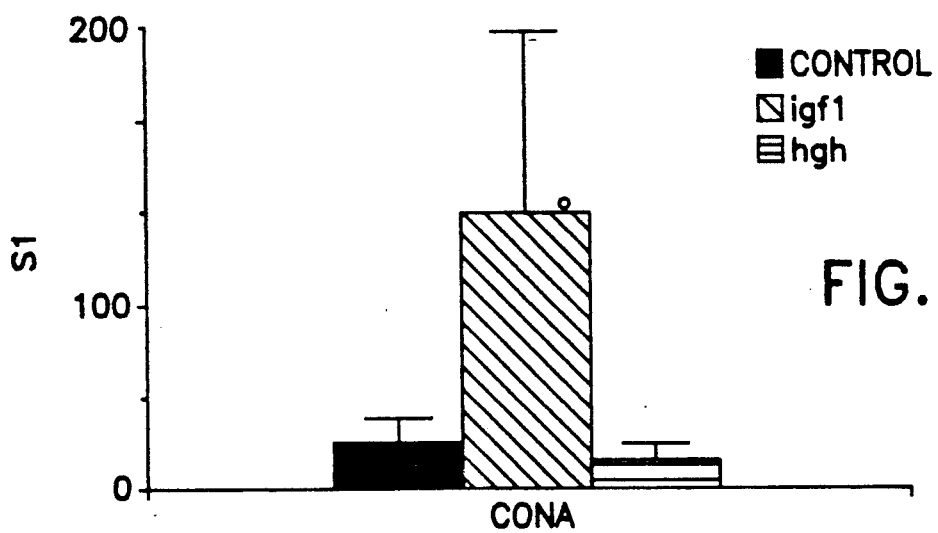
FIG. 10 represents a graph of the mitogenic responses 14 days after initial excipient or IGF-I or hGH treatment of mice using the mitogens LPS (FIG. 10A), Con A (FIG. 10B), or PWM (FIG. 10C).
Figure 10B:
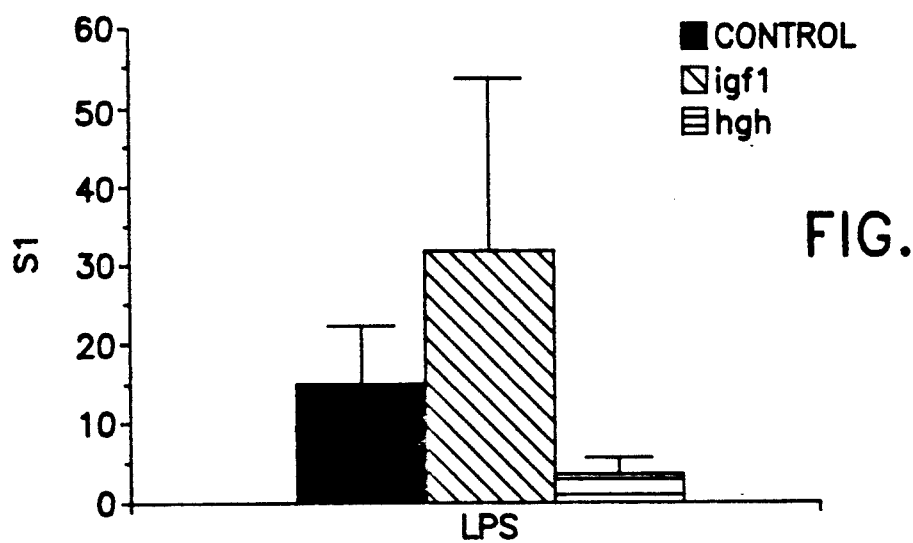
Figure 10C:
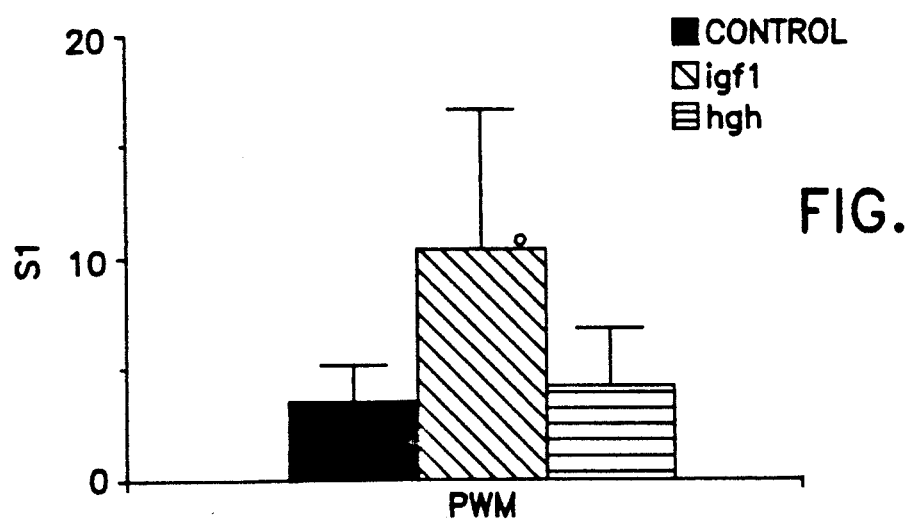

In contrast to the decreased response seen at 7 days, following 14 days of IGF-I treatment the mitogenic response of splenocytes from IGF-I-treated mice was significantly elevated compared to controls (FIG. 10). These data suggest that short-term administration of IGF-I results in significant increases in lymphocyte number, but additional time is required to see alterations in lymphocyte responsiveness.

3. Effect of Combination After 14-Day Treatment a. Simultaneous Treatment

Figure 12:
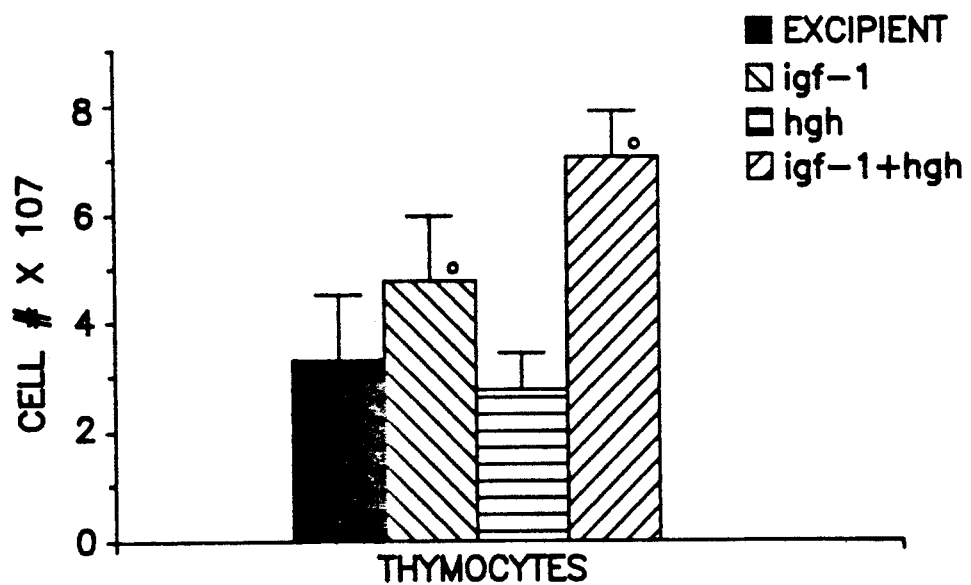
FIG. 12 represents a graph of the number of thymocytes after 14-day IGF-I treatment, hGH treatment, and IGF-I plus hGH treatment.
Figure 11A:
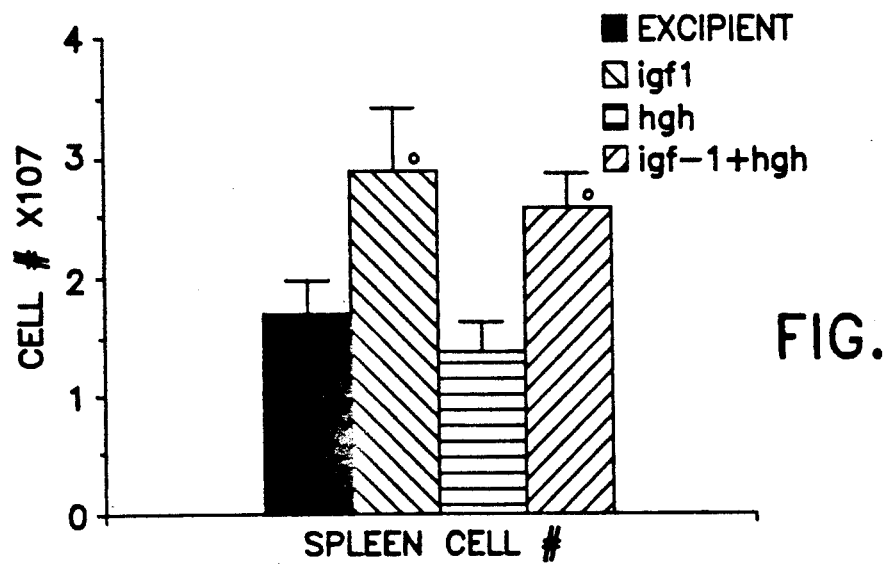
FIGS. 11A, 11B, and 11C provide graphs on the splenocyte number, splenic T-cell population number, and splenic B-cell number, respectively, after 14-day treatment with excipient, IGF-I, hGH, and IGF-I plus hGH.
Figure 11B:
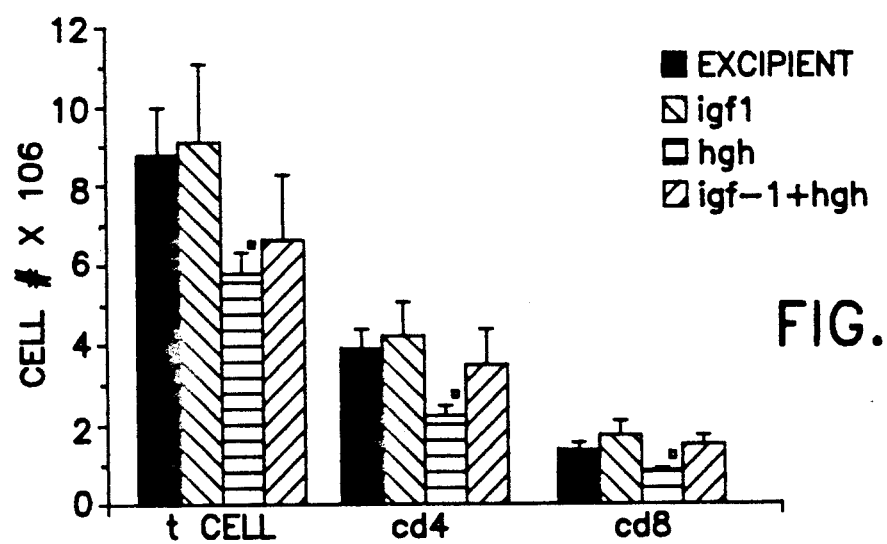
Figure 11C:
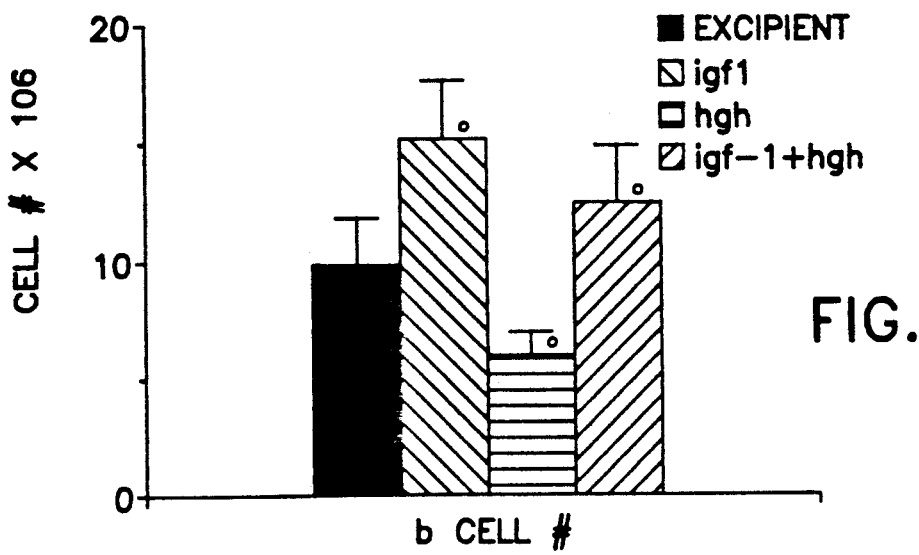

Since hGH and IGF-I had different effects on lymphocyte populations, in the next series of experiments the effects of hGH administered simultaneously with IGF-I were examined. Whether alone or in combination with sc-injected hGH, IGF-I treatment produced increases in total lymphocyte number in the spleen, which again appeared to be due primarily to an increase in B-cell number (FIG. 11). The combination of IGF-I and hGH did have a pronounced effect on thymocyte number over IGF-I or hGH treatment alone (FIG. 12).

It is expected that the preferred route of combination therapy would be administration of continuously infused IGF-I and hGH.

b. Sequential Treatment

When GH (at 280 μg/day) was administered first for 14 days followed by administration by IGF-I (at 140 μg/day) for 14 days, no effect of IGF-I was seen.

4. Long-Term Effects of 14-Day Treatment

To determine the long-lasting effects of IGF-I, hGH and the combination, lymphocyte populations from control and treated animals were examined 7 and 21 days after 14-day treatment with hGH, IGF-I, or the combination of IGF-I and hGH.

Figure 13A:
FIGS. 13A, 13B, and 13C represent graphs of splenic lymphocyte number, splenic T-cell subpopulation number, and splenic B-cell number, respectively, 7 days after the end of excipient, IGF-I, hGH, and IGF-I plus hGH treatment.
Figure 13B:
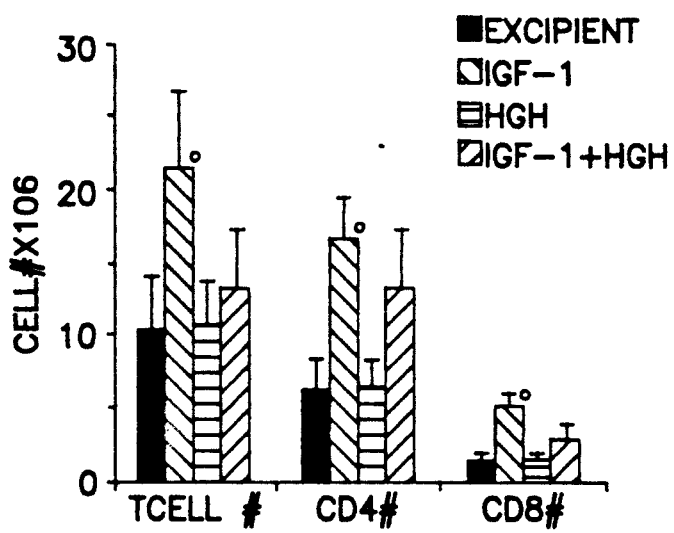
Figure 13C:
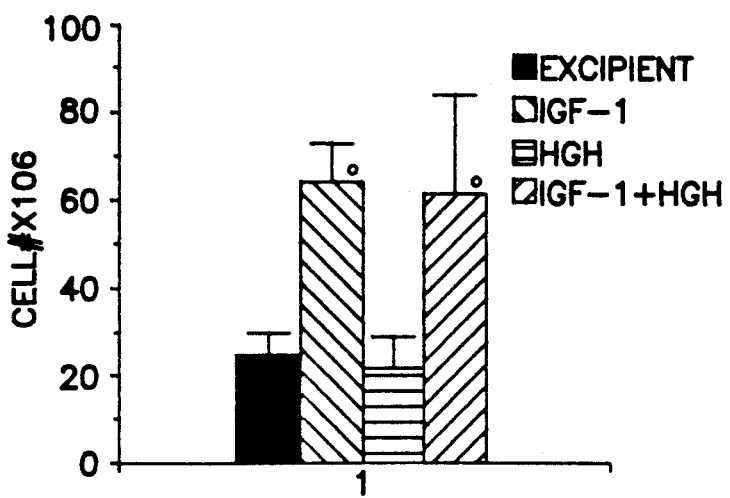
Figure 14:
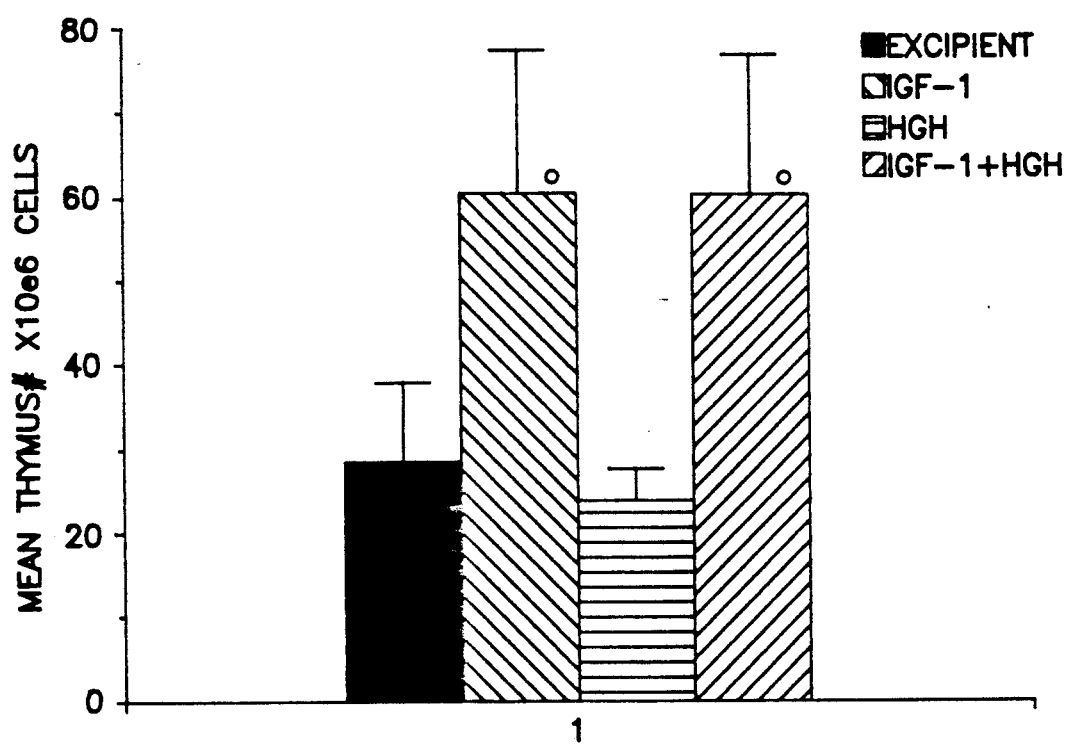
FIG. 14 represents a graph of the number of thymocytes 7 days after the end of excipient, IGF-I, hGH, and IGF-I plus hGH treatment.
Figure 16A:
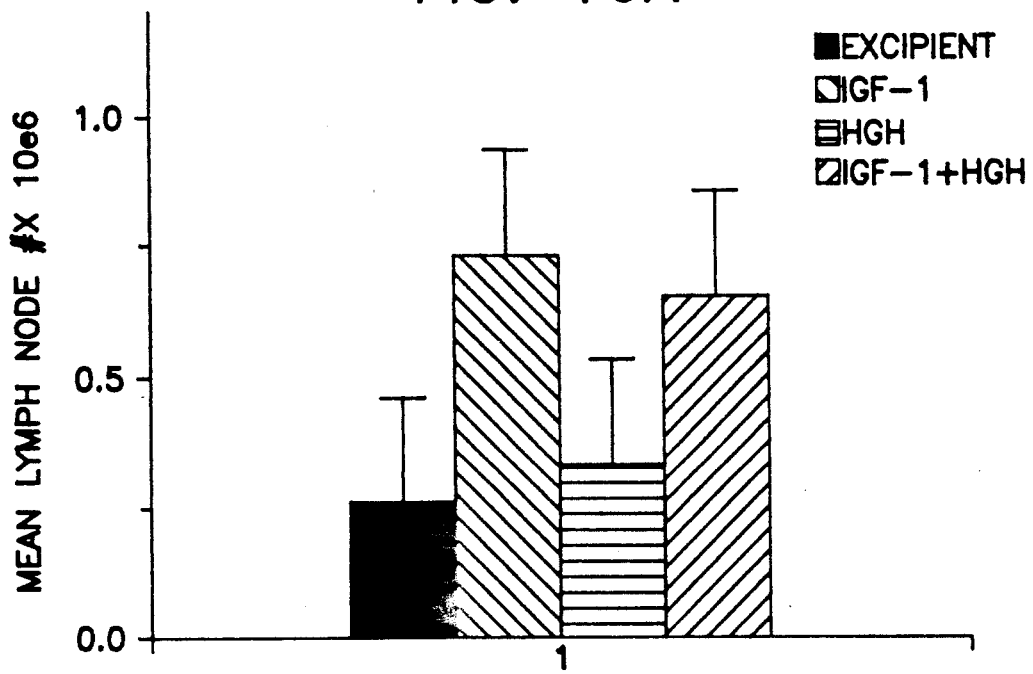
FIGS. 16A and 16B represent graphs of the lymph node cell number and lymph node T-cell populations, respectively, 7 days after the end of excipient, IGF-I, hGH, and IGF-I plus hGH treatment.
Figure 16B:
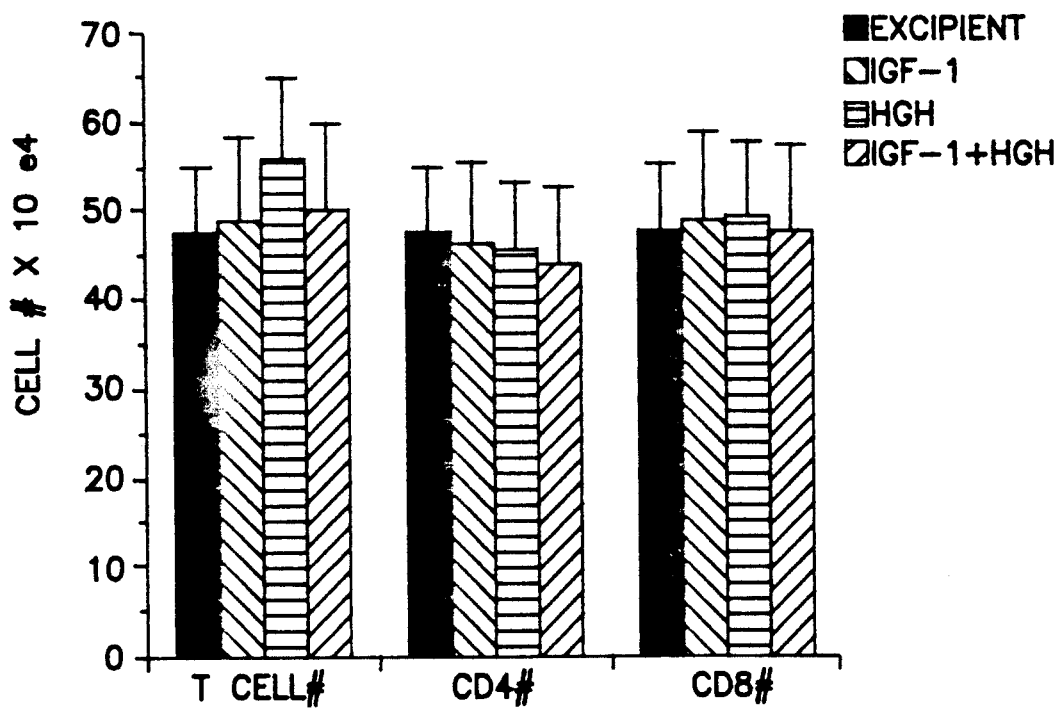

Seven days post-treatment the IGF-I- and IGF-I-plus hGH-treated mice had significantly elevated splenocyte numbers compared to either control, or hGH-treated mice (FIG. 13). A statistical increase in B-cell number was observed in both IGF-I-treated groups. The increase in T-cell number was significant in the IGF-I only group, but not in the combination of hGH plus IGF-I group. Furthermore, both CD+and CDs+T-cell populations were elevated in this group compared to controls. As was the case with 14-day treatment, both groups of IGF-I-treated mice had elevated thymocyte numbers compared to hGH-treated or control mice (FIG. 14). In addition, IGF-I, alone or in combination with hGH, produced an increase in peripheral lymph node cell numbers (FIG. 16). No alteration in node T cell number or $CD_4:CD_8$ ratios was observed following these treatment regimes.

Figure 15A:
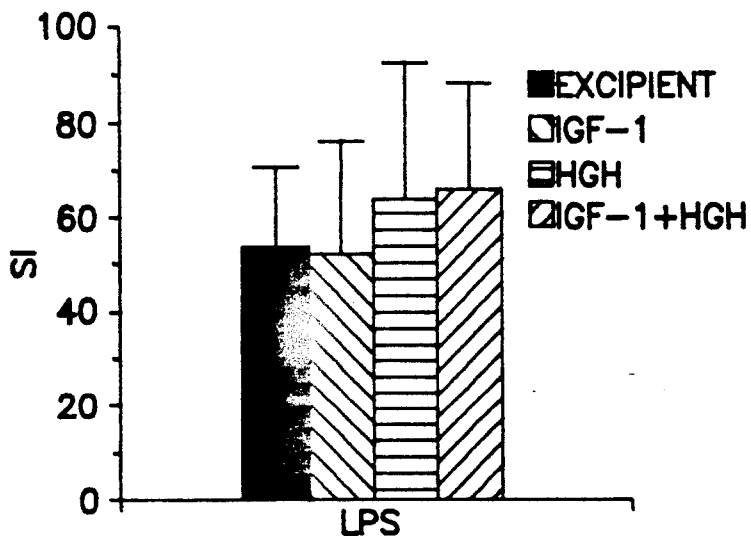
FIG. 15 represents a graph of the mitogenic responses 7 days after the end of excipient, IGF-I, hGH, or IGF-I plus hGH treatment of mice using the mitogens LPS (FIG. 15A), Con A (FIG. 15B), or pWM (FIG. 15C).
Figure 15B:
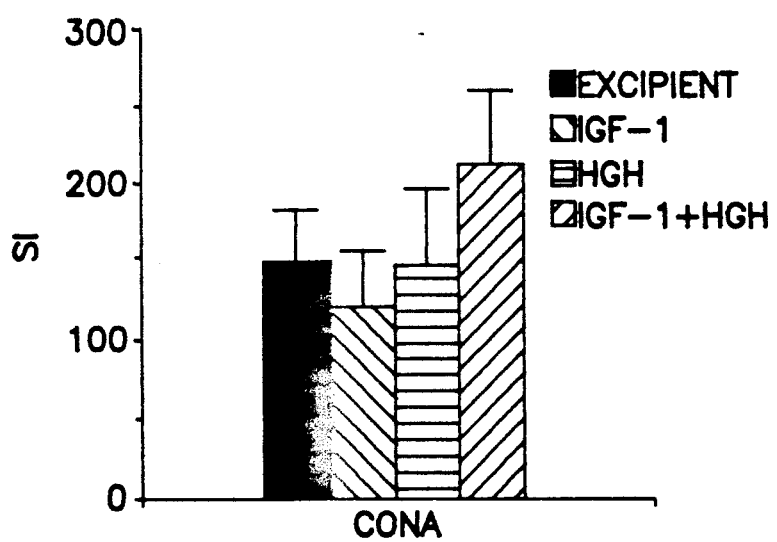
Figure 15C:
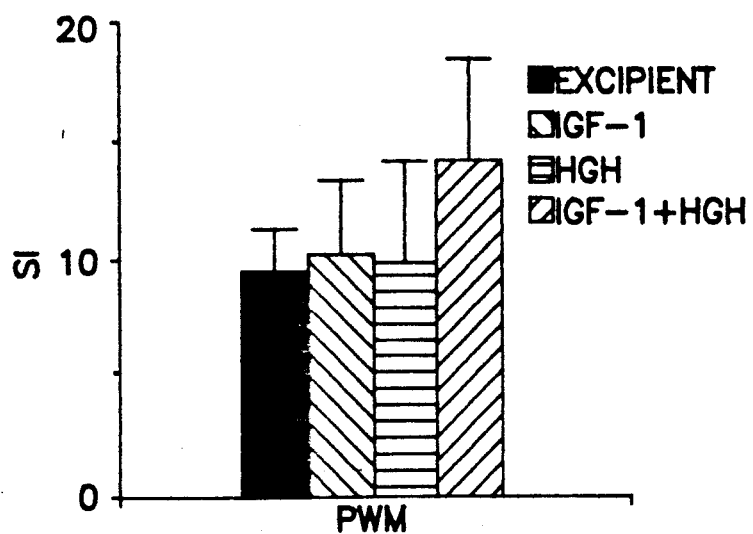

Unlike the enhanced proliferative response to mitogens seen at 14 days of treatment, the mitogenic responses of the IGF-I-treated mice had returned to control values by 7 days after treatment (FIG. 15). The largest mitogenic responses were seen in the hGH- plus IGF-I-treated group compared to controls, but these differences were not statistically significant.

Figure 17A:
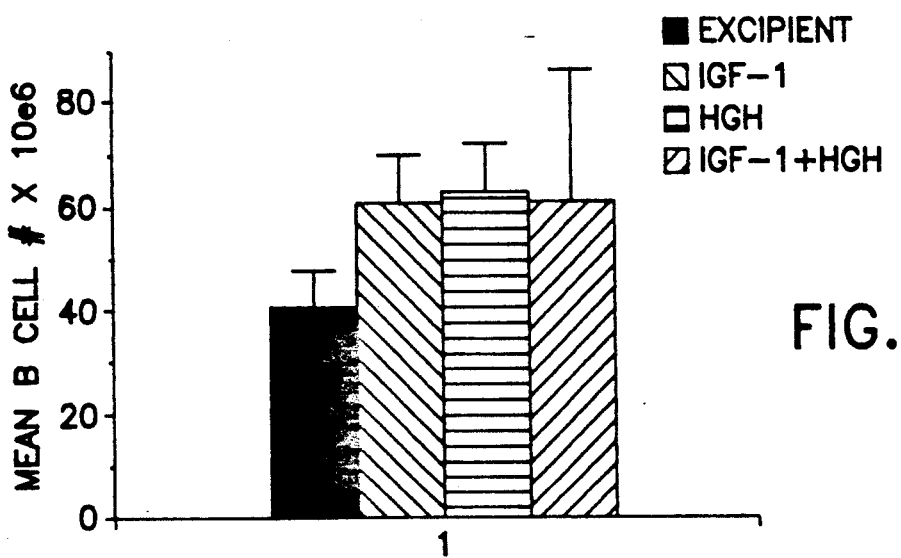
FIGS. 17A, 17B, and 17C provide graphs on the splenic lymphocyte number, splenic T-cell population number, and splenic B-cell number, respectively, 21 days after the end of excipient, IGF-I, hGH, and IGF-I plus hGH treatment.
Figure 17B:
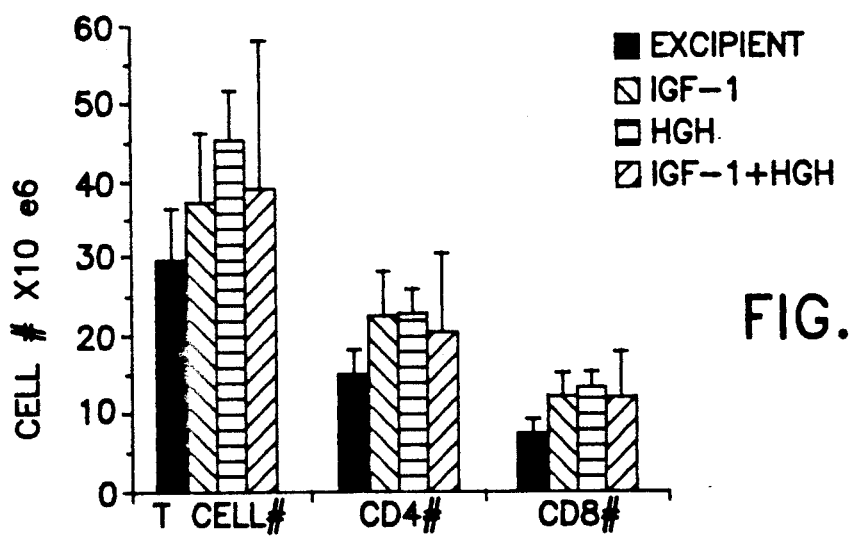
Figure 17C:
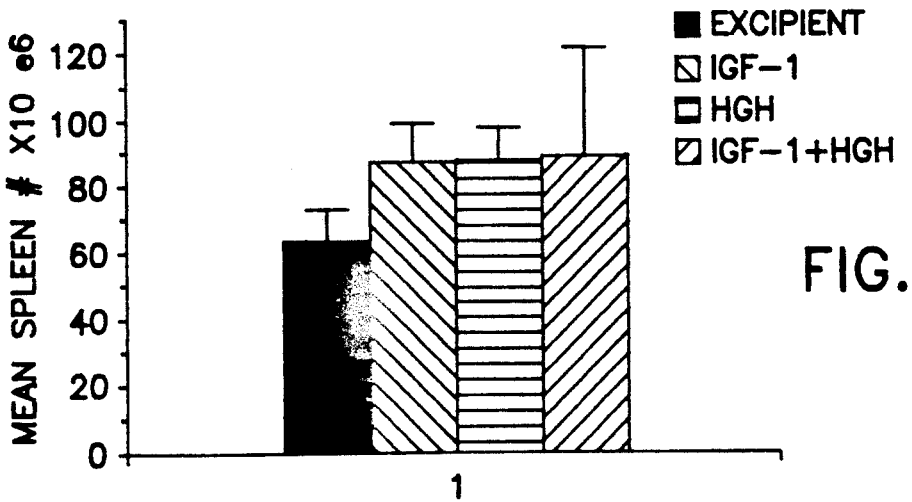
Figure 18:
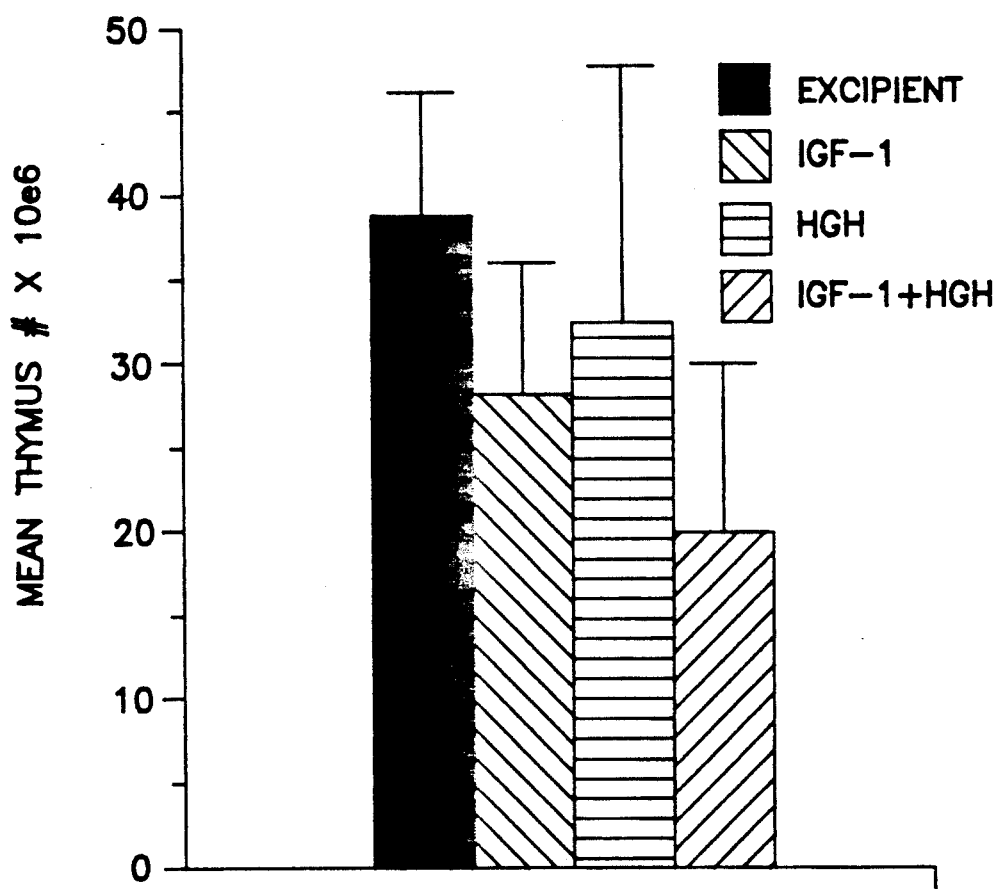
FIG. 18 represents a graph of the number of thymocytes 21 days after the end of excipient, IGF-I, hGH, and IGF-I plus hGH treatment.

By 21 days after treatment, all four groups of mice had equivalent splenocyte (FIG. 17) and thymocyte (FIG. 18) numbers. Thus, 21 days appears to be sufficient to restore the normal cell number and phenotypic ratios following IGF-I treatment.

Figure 19A:
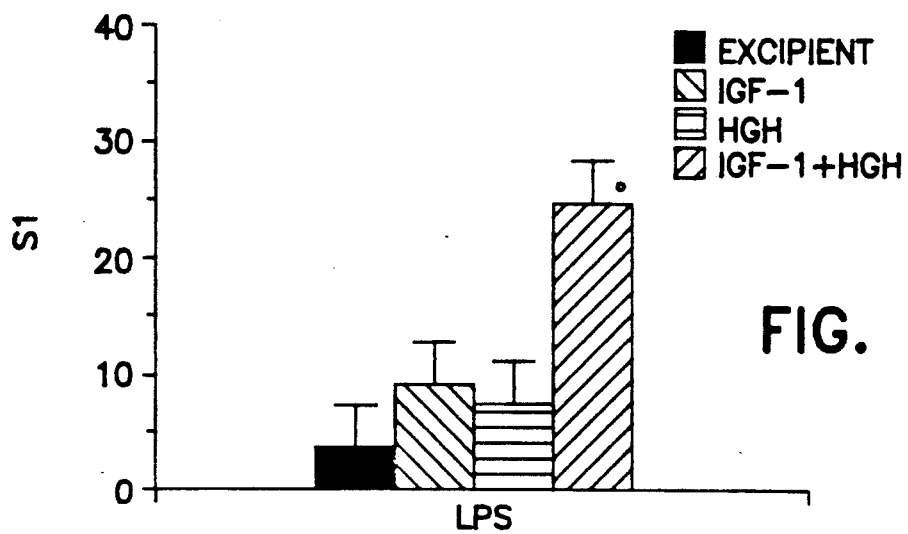
FIG. 19 represents a graph of the mitogenic responses 21 days after the end of excipient, IGF-I, hGH, or IGF-I plus hGH treatment of mice using the mitogens LPS (FIG. 19A), Con A (FIG. 19B), or PWM (FIG. 19C).
Figure 19B:
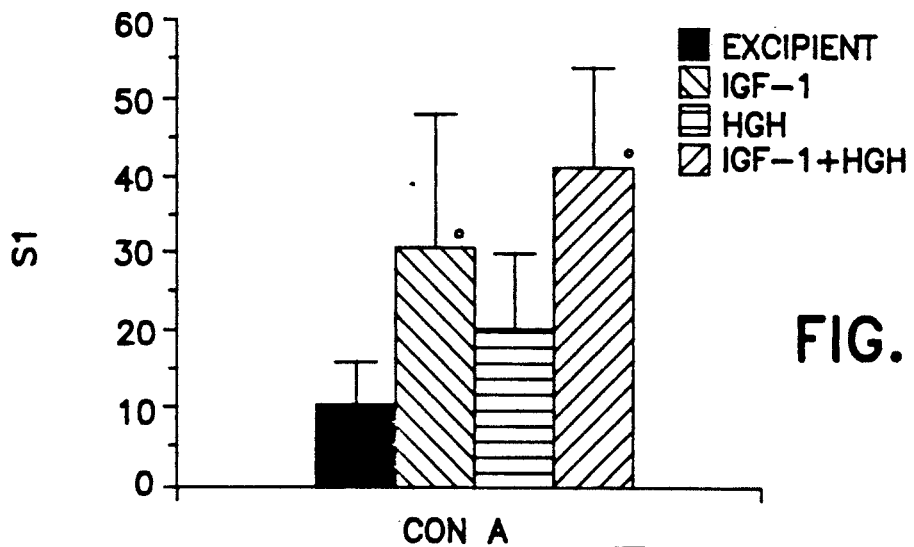
Figure 19C:
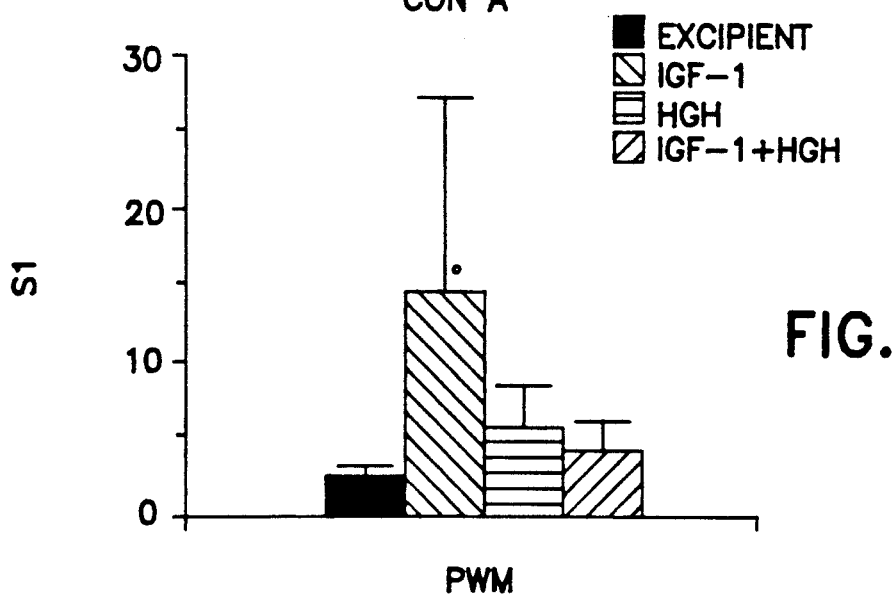

However, by 21 days after treatment, both the LPS and Con A responses of the hGH- plus IGF-I-treated group were statistically elevated compared to controls (FIG. 19). Similarly, the responses to all three mitogens were elevated in the IGF-I only group. These results suggest that IGF-I has an early and late acting effect on lymphocyte responses, while the combination of IGF-I and hGH appears to require some time to effect lymphocyte responsiveness. sc-Injected hGH alone failed to have a statistically significant effect on mitogen responses at any time point examined.

EXAMPLE II

Response to Antigen in Secondary Immunization

The purpose of this experiment was to evaluate the immune function in male mice (retired breeders) immunized with dinitrophenyl-ovalbumin and treated with IGF-I. Previous experiments indicated that 14 days of continuous IGF-I administration to retired male breeder mice increased the body weight, spleen, and thymus organ weights. It was shown that the increase in spleen weight was attributable to an increase in B-cell number and an increase in mitogen responsiveness. It was also shown that increased T-cell numbers in the thymus could be generated and that these cells were also more responsive to mitogens. These data indicated that if IGF-I caused the antibody-producing B-cells and the helper T-cells to be greater in number and more responsive to mitogens, then IGF-I might be able to give a greater antibody response to an antigen.

I. Protocol

Forty-eight hours after arrival, all animals received a single ip injection (100 μl) of dinitrophenyl-ovalbumin mixed with alum (DNPOA). (The dinitrophenyl group is a hapten that elicits a B-cell-dependent response, and the ovalbumin is a carrier that elicits a T-cell dependent response.) The DNPOA was mixed before use by adding 50 μl of DNPOA (1 mg/ml) to 2.45 ml of sterile PBS, pH 7.0 and 2.50 ml of aluminum hydroxide absorptive gel (Rehsorptar ™ brand, sold by Armor Pharmaceutical Col, IL, 20 mg/ml). The DNPOA was mixed for approximately 30 minutes prior to injection. The day of DNPOA immunization is designated as Day 0.

At Day:19, ten animals were grouped by body weight into two groups. (One animal was found dead on day 9.). Nineteen miniosmotic pumps (Alzet Corp., Palo Alto, Calif.) model 2002 (0.5 μl/hr, 14 days) were filled with IGF-I excipient or IGF-I as described in Example I and placed in sterile saline solution overnight at 4° C.

At Day 20, five randomly selected animals were bled (orbitally). Serum was analyzed for IgG specific to DNPOA, as described below.

At Day 20, all ten animals were anesthetized with an ip injection of approximately 0.5 ml of avertin as described above. The animals were clipped free of hair on a dorsal area of approximately 2 cm² and wiped with 70% alcohol. A small incision, approximately 1 cm, was made in the clipped area. A hemostat was inserted into the incision and pushed anteriorly to the base of the tail and the above-described minipumps were inserted. Five animals were implanted with two minipumps each of excipient buffer. Five animals were implanted with two minipumps each of IGF-I. The rate of delivery for the minipumps gave an IGF-I dose of 120 μg IGF-I/day for maximum of 14 days. After recovery from anesthesia, five animals each from the excipient and IGF-I groups received a booster ip 100-μl injection of DNPOA.

At Day 25, one animal in the excipient group was found dead.

At Day 34, all nine animals were bled orbitally and the serum was analyzed for IgG.

See Table V for the overall immunization scheme.

II. Assay of Anti-DNP Antibodies

IgG: IgG anti-DNP antibodies in the test mouse sera were measured by ELISA (enzyme-linked immunoassay) using serum of anti-DNPOA primed mice as a reference standard. The ELISA was set up in 96-well plates. Each well was coated with 0.1 ml of 2.5 μg/ml DNP₆HSA (dinitrophenyl human serum albumin) for 24 hours at 4° C.

TABLE V

| Retired Male Breeder Mice (BALB/c) Immunized with DNPOA | | | |
|---|---|---|---|
| Group | Number | 1st Injection DNPOA | Compound (implant date) | 2nd Injection DNPOA |
| 1 | 4 | Day 0 | Excipient Day 20 | Day 20 |
| 2 | 5 | Day 0 | IGF-I Day 20 | Day 20 |

After blocking with 0.1% BSA, 0.1 ml of each test sera was added to the antigen-coated plates in triplicate and the plates were incubated for two hours at room temperature. The plates were washed three times with PBS/0.02% Tween 20, and 0.1 ml of 1:2000 dilution of rabbit anti-mouse IgG (Cappel Labs) was added to each well. Plates were again incubated two hours and washed. Next, 0.1 ml of 1:1600 dilution of goat anti-rabbit horseradish peroxidase conjugated antiserum was then added to each well for one hour at room temperature. After washing, 0.1 ml of 0.2 mg/ml orthophenylene diamine (OPD), 0.01% hydrogen peroxide in 0.05M citrate buffer was added to each well, the reaction was stopped with 2M sulfuric acid after 30 minutes, and the optical density was read at 490 nm on a Microtect plate reader.

III. Assay of Total IoG

IgG antibodies in the test mouse sera were measured by an ELISA using murine IgG as a reference standard. The ELISA was set up in 96-well plates. Each well was coated with 0.1 ml of 1:200 goat anti-murine IgG-Fc specific.(Cappel Labs, Westchester, PA) for 24 hours at 4° C. After blocking with 0.1% BSA, 0.1 ml of each test sera was added to the antibody-coated plates in triplicate and the plates were incubated for 2 hours at room temperature. The plates were washed three times with PBS/0.02% Tween 20, and 0.1 ml of 1:250 dilution of horseradish peroxidase-conjugated Fab-specific goat-anti-mouse IgG (Cappel Labs) was added to each well. Plates were again incubated two hours and washed. After washing, 0.1 ml of 0.2 mg/ml OPD, 0.01% hydrogen peroxide in 0.05M citrate buffer was added to each well, the reaction was stopped with 2M hydrogen peroxide after 30 minutes, and the optical density was read at 490 nm on a Microtect plate reader.

IV. Results

Figure 20A:
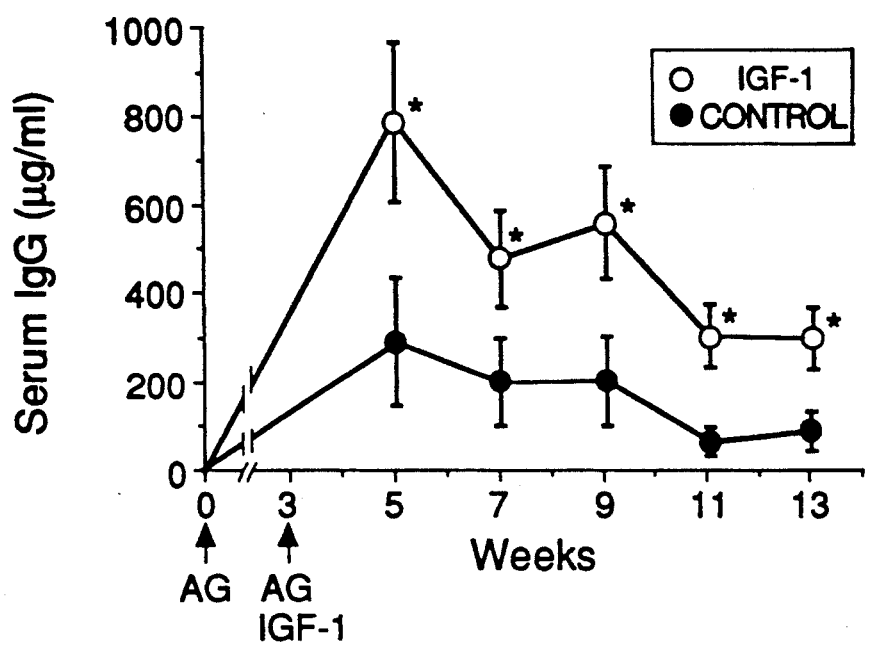
FIG. 20 shows the concentration of anti-dinitrophenyl-ovalbumin IgG (FIG. 20A) and total IgG (FIG. 20B) in $\mu g/ml$ in the serum of mice as a function of the number of weeks since the first immunization with dinitrophenyl-ovalbumin conjugate (Day 0, designated AG), wherein at week 3 (Day 20) the mice were boosted with conjugate and given excipient or IGF-I.
Figure 20B:
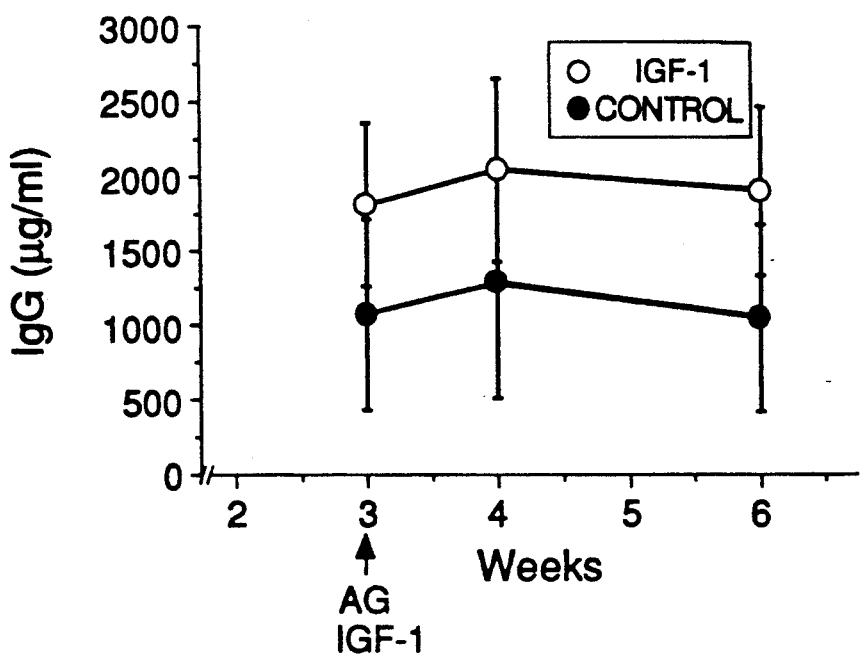

FIG. 20 shows the concentration of total (FIG. 20B) and OA-specific (FIG. 20A) IgG in the serum of excipient- or IGF-I-treated mice. IGF-I treatment significantly increased the secondary IgG response to antigen at every time point examined. While there was a trend toward elevation in total IgG levels in the IGF-I group, the values were not statistically increased compared to controls. Thus, IGF-I functions to boost the memory response of the mammal. It is noted that exposure to IgG after a secondary immunization produces a longer improvement in antibody production.

EXAMPLE III

Effect on Immune Response After Bone Marrow Transplantation

The purpose of this experiment is to determine the effects of IGF-I treatment of mice on repopulation of the spleen and thymus following bone marrow transplantation.

I. Protocol

Male BALB/c mice, 19–26 g and 6–7 weeks old (Charles River, San Diego, Calif.), were used in the study. The animals were group housed in polypropylene cages with food (Purina Rodent Chow 5010, St. Louis, Mo.) and water, ad libitum. All animals were weighed the day of pump implantation and randomized into groups. Animals were identified by stainless-steel ear tags.

Ten animals per group were studied. Animals were anesthetized with an ip injection of approximately 0.4 ml of avertin prior to implantation of Alzet osmotic minipumps Model 2002 (0.58±0.03 μl/hr./14 days) filled with IGF excipient or 200 μl of rIGF-I described above diluted to achieve a daily, continuous delivery of approximately 40 or 120 μg/day/14 days.

Daily animal weights were recorded. Twenty-four hours after the implant, all animals were irradiated with 900 rads of radiation from $^{137}$Cesium (4.29 minutes). Within one hour after irradiation animals received an intravenous injection of $1 \times 10^7$ bone marrow cells (250 µl).

Femurs and tibias were removed from 40 donor animals. The bone marrow was flushed out with PBS. Cells were centrifuged and washed with saline. Viable cells were counted and diluted with saline to achieve $10^7$ cell/0.25 ml.

One half of the animals were sacrificed 14 days after the irradiation treatment. All the surviving animals from the group that was irradiated and received no bone marrow were sacrificed at this time. The remaining animals were sacrificed 23 days after the irradiation treatment. Spleens, thymuses, livers, and hearts were removed and weighed. Long bones were taken for histology and the spleens and thymuses retained for cytological and in vitro assays. Blood was taken for analysis of peripheral cytology. The protocol is given in Table VI.

TABLE VI

| Group | (n) | Route | Dose of IGF-I (µg/day) | |
|---|---|---|---|---|
| 1 | 10 | sc pump | 0 | no marrow |
| 2 | 10 | sc pump | 0 | received marrow |
| 3 | 10 | sc pump | 40 | received marrow |
| 4 | 10 | sc pump | 120 | received marrow |

II. Results
A. Weight Gain

Animals not replaced with bone marrow showed a high mortality, where three out of ten animals survived for 14 days. For all measures (blood, tissue, and whole body) this group of animals showed the expected effect of a lethal dose of radiation.

Animals replaced with bone marrow survived with only two animals out of 30 dying over the 23-day study. The actual weight gains in the four groups are shown in Table VII.

TABLE VII

| | WEIGHT GAINS | | | |
|---|---|---|---|---|
| | Thymus Weight (g) | | Spleen Weight (g) | |
| | Day 14 | Day 23 | Day 14 | Day 23 |
| No marrow | 8.6 ± 0.9 | — | 18.6 ± 2.5 | — |
| Marrow only | 12.6 ± 1.0 | 26.0 ± 12.9 | 77.8 ± 31.5 | 74.0 ± 29.0 |
| IGF-I low | 23.5 ± 6.2 | 36.4 ± 9.2 | 101.2 ± 20.5 | 92.0 ± 8.3 |
| IGF-I high | 27.3 ± 10.9* | 51.2 ± 9.3** | 125.0 ± 35.4* | 103.6 ± 19.4 |

*p < 0.05 of Marrow Only on same day
**p < 0.01

There was a clear effect of IGF-I increasing thymus and spleen weight in this model. It appeared that the thymic effect was greater that the splenic effect, as there was a maintained doubling of thymus size in the high-dose IGF-I group, with the effect on the spleen initially being statistically significant, but not maintained at day 23. There was no overall effect of treatment on liver or heart weight.

The dramatic whole body anabolic effect of IGF-I in this setting confirms that IGF-I continues to be anabolic on the whole body. The effect of IGF-I increasing the mass of the thymus and spleen was surprising in the very extreme setting of immune deficiency that this model presents. It might be expected in other models of immune deficiency, i.e., AIDS, that IGF-I would also show these remarkable efficacies.

The body weight changes for all four groups are shown in FIG. 21. The figure shows clearly the very large weight loss in the animals following radiation exposure. There was a clear dose-related effect of IGF-I protecting the mice from this catabolism. High-dose IGF-I had a significant anabolic effect as early as seven days following treatment and this effect persisted to the end of the study. Low-dose IGF-I also caused a significant protection at some time points ($p < 0.05$).

B. Cell Numbers and Mitogenic Responses

Figure 22A:
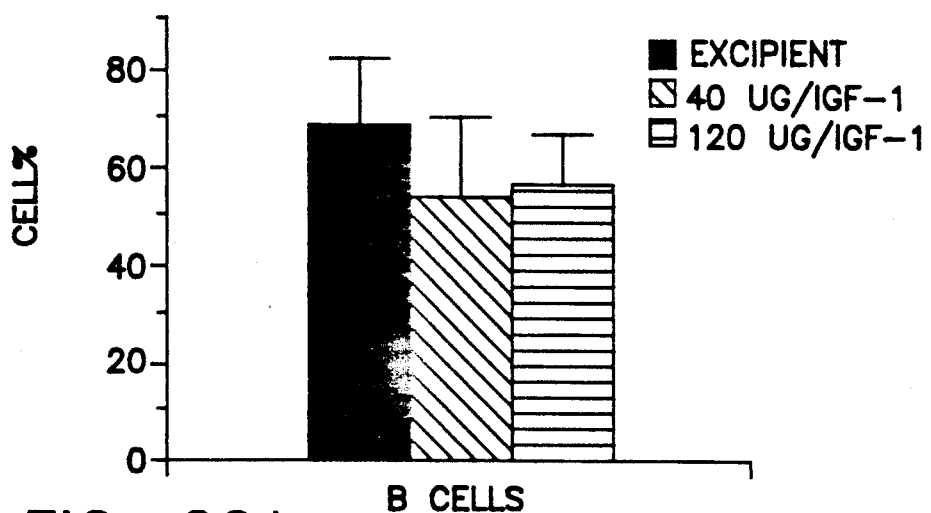
FIGS. 22A, 22B, and 22C show graphs of peripheral blood lymphocyte B-cells, T-cell subpopulations, and H/S ratio, respectively, 14 days after irradiation of mice with transplanted bone marrow and treated with excipient, 40 $\mu g$ IGF-I, or 120 $\mu g$ IGF-I.
Figure 22B:
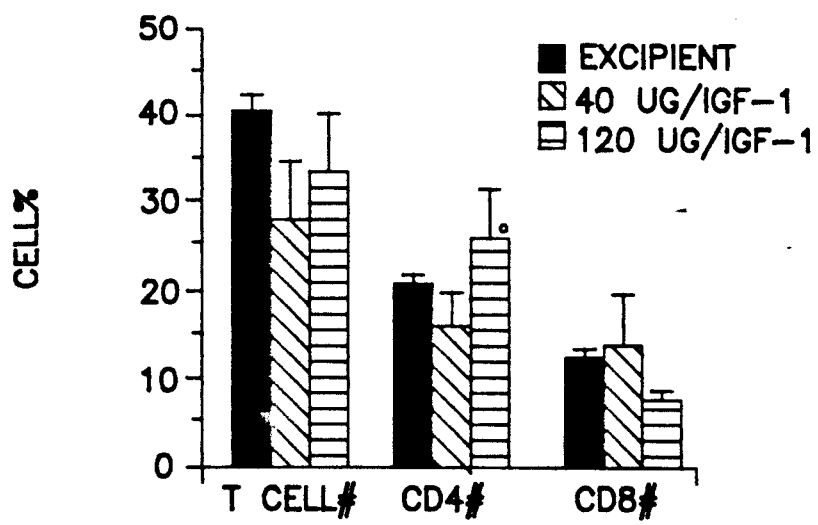
Figure 22C:
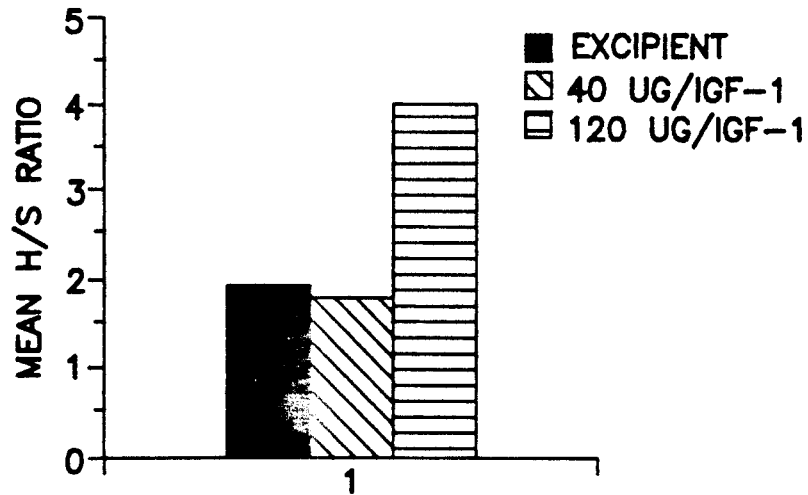

Fourteen days post irradiation, animals receiving 120 µg IGF-I had increased numbers of $CD_4$+T-cells in the peripheral blood compared to control or low-dose IGF-I treatment (FIG. 22). Indeed, the ratio of $CD_4$ to $CD_5$ increased from 2 to 4 in this treatment group compared to controls. These data are consistent with the preferential increases in $CD_4$ cells seen in the spleens of aged mice treated with IGF-I for 7 or 14 days. No effect was seen on peripheral B-cell number following IGF-I treatment.

Figure 23A:
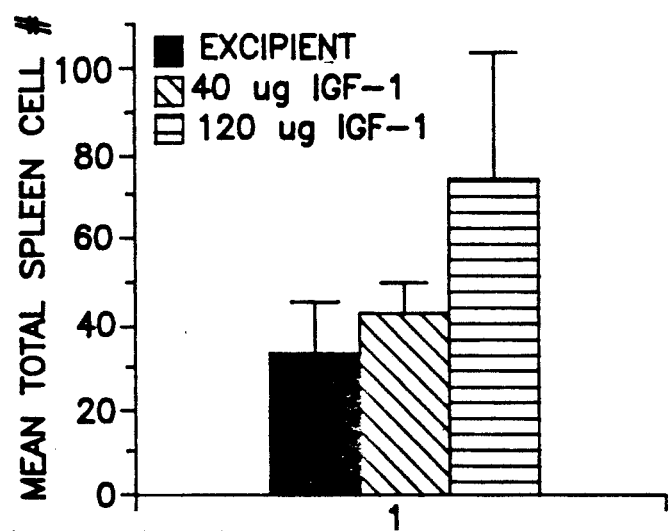
FIGS. 23A, 23B, and 23C show graphs of splenic lymphocyte number, splenic T-cell subpopulations and splenic B-cell number, respectively, 14 days after irradiation of mice with transplanted bone marrow and treated with excipient, 40 $\mu g$ IGF-I, or 120 $\mu g$ IGF-I.
Figure 23B:
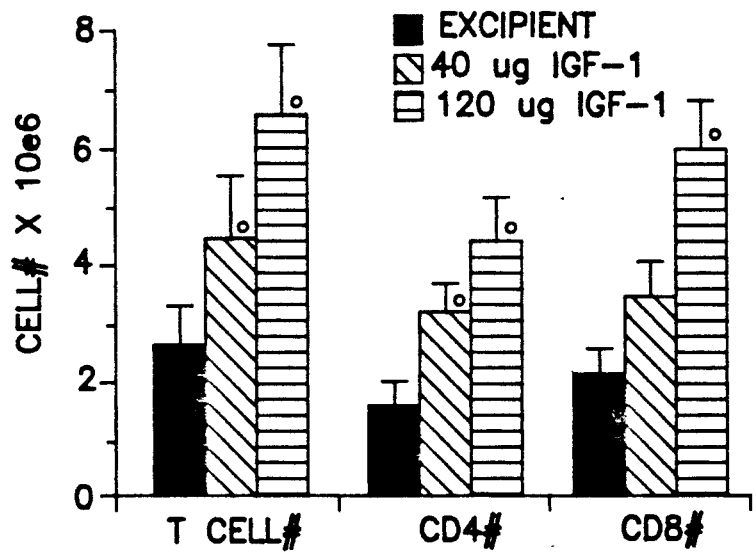
Figure 23C:
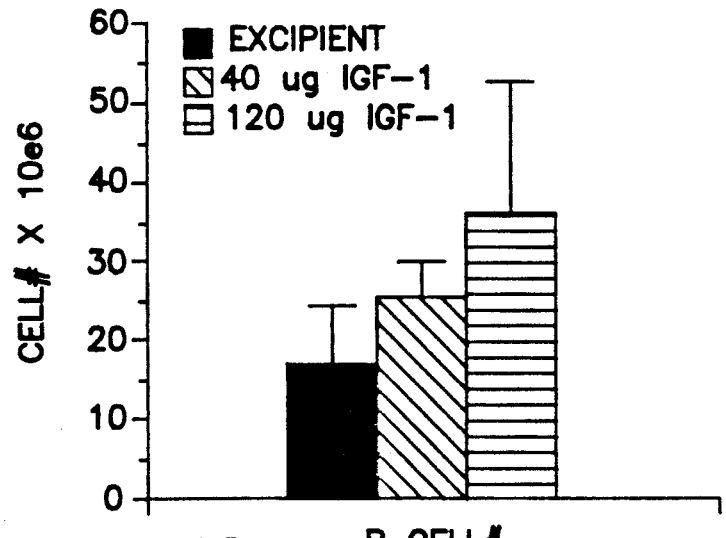
Figure 24A:
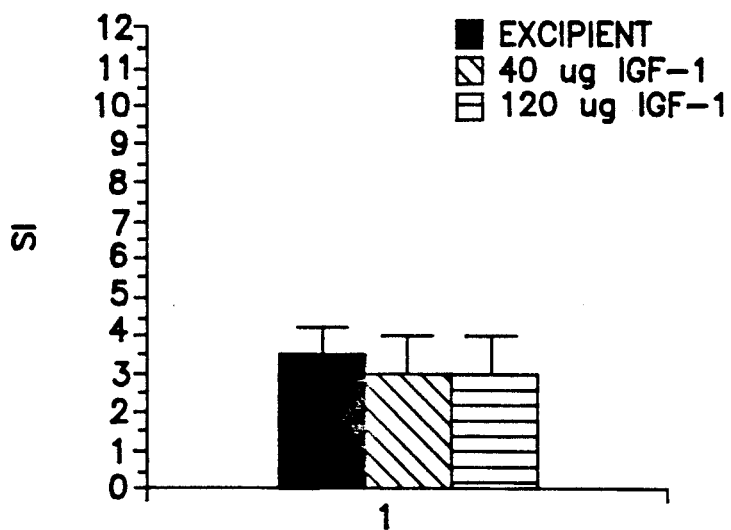
FIG. 24 represents a graph of the mitogenic responses 14 days after irradiation of mice with transplanted bone marrow and treated with excipient, 40 $\mu g$ IGF-I, or 120 $\mu g$ IGF-I using the mitogens LPS (FIG. 24A), Con A (FIG. 24B), or PWM (FIG. 24C).
Figure 24B:
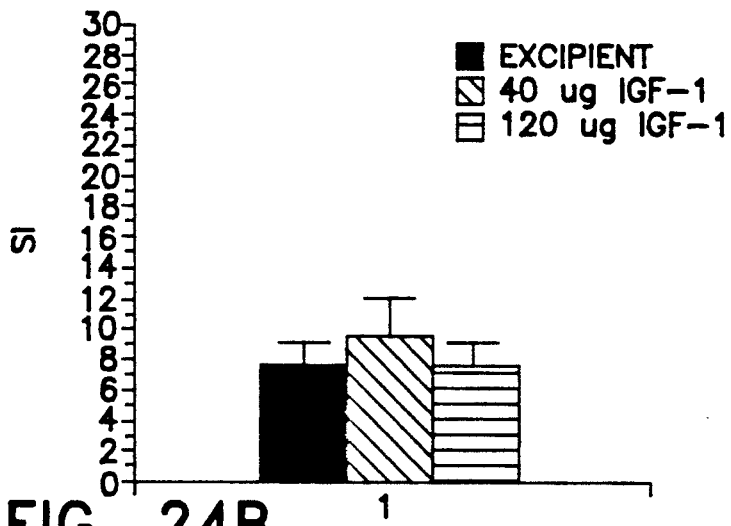
Figure 24C:
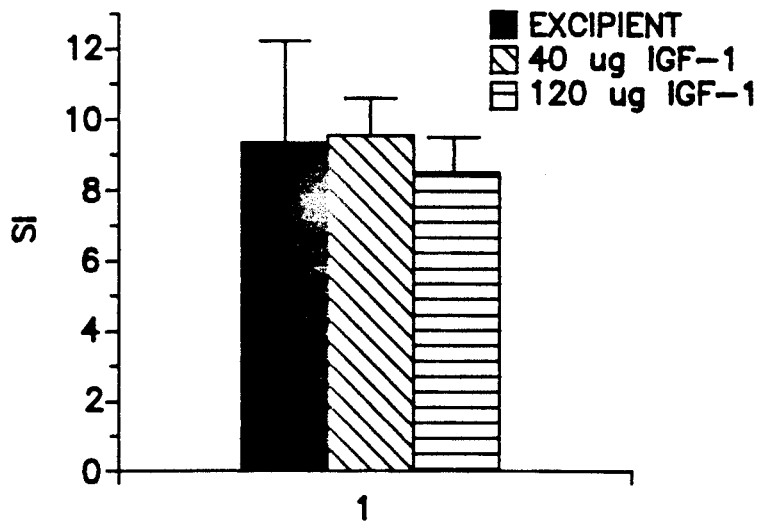

When the splenic lymphocytes from these animals were quantitated by FACS analysis, IGF-I treatment was shown to produce a dose-responsive increase in the number of T- and B-cells (FIG. 23). However, no effect was seen on mitogenic responsiveness of these splenocytes when measured at this time point (FIG. 24).

Figure 28A:
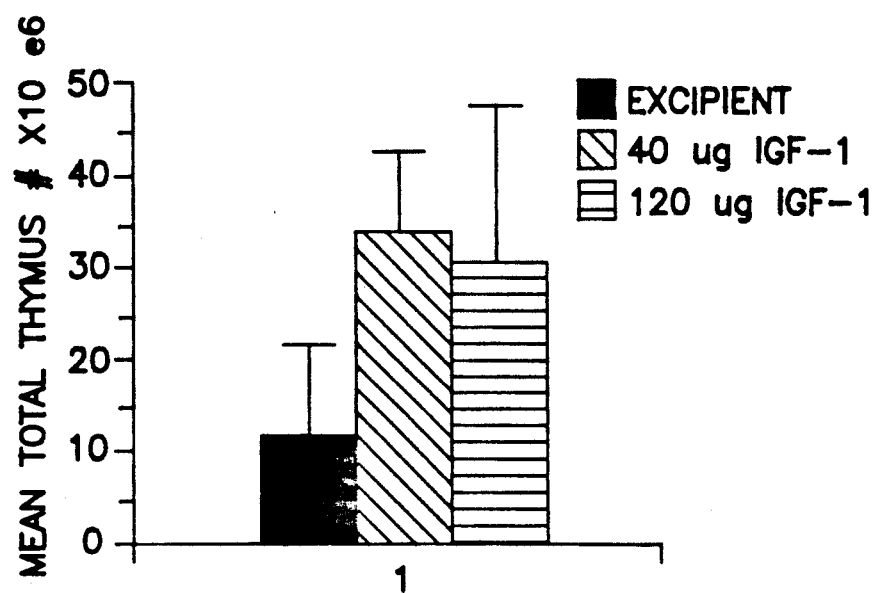
FIG. 28 represents a graph of thymic lymphocyte number 14 days (FIG. 28A) or 21 days (FIG. 28B) after irradiation of mice with transplanted bone marrow and treated with excipient, 40 $\mu g$ IGF-I, or 120 $\mu g$ IGF-I.
Figure 28B:
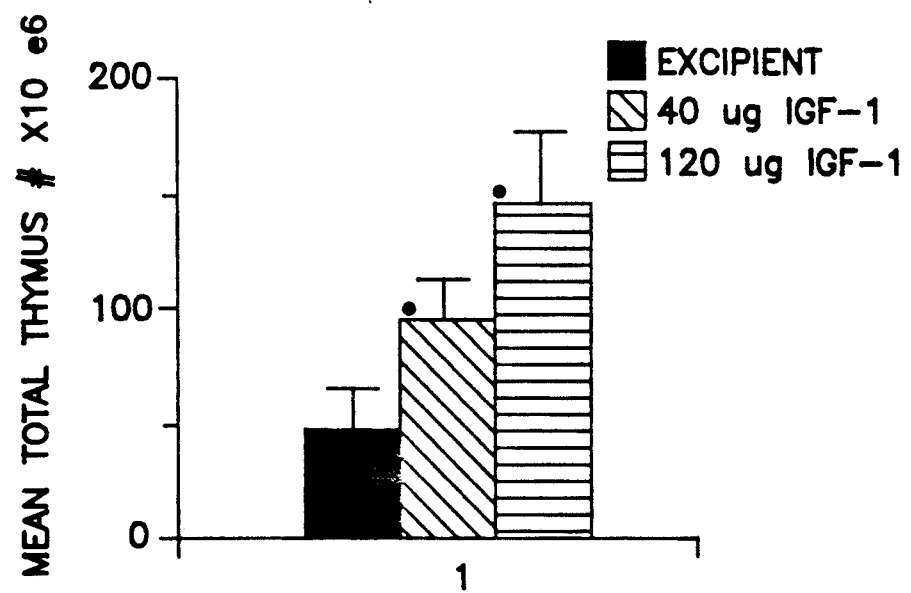

As was the case with the spleen, the number of lymphocytes repopulating the thymus of the IGF-I mice was increased compared to controls (FIG. 28).

Figure 25A:
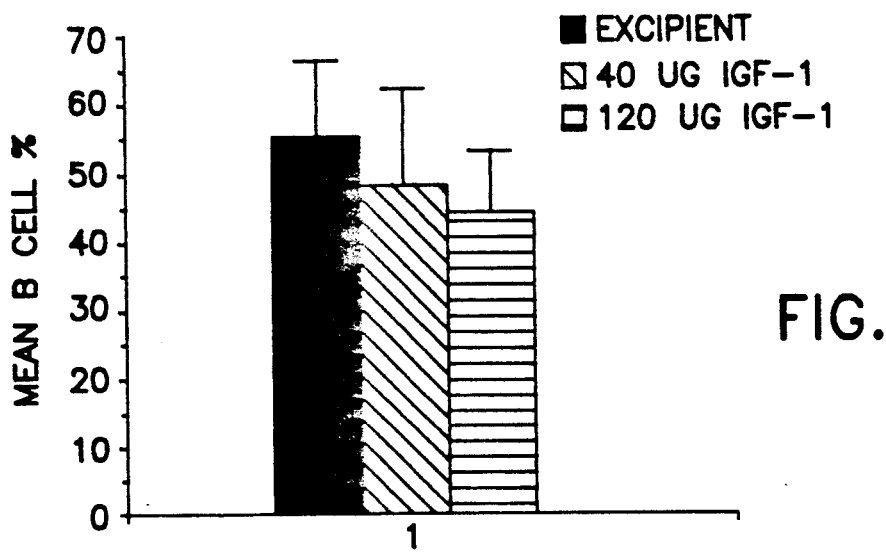
FIGS. 25A, 25B, and 25C show graphs of peripheral blood lymphocyte B-cells, T-cell subpopulations, and H/S ratio, respectively, 21 days after irradiation of mice with transplanted bone marrow and treated with excipient, 40 $\mu g$ IGF-I, or 120 $\mu g$ IGF-I.
Figure 25B:
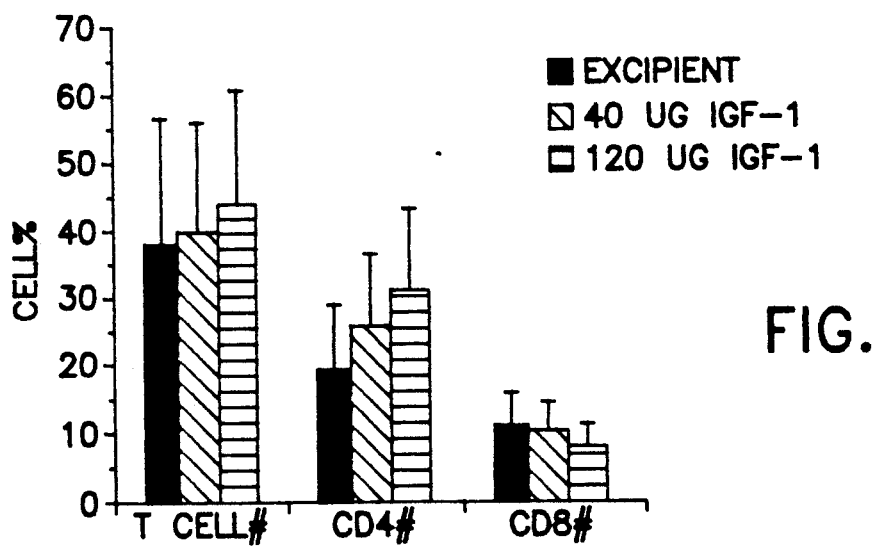
Figure 25C:
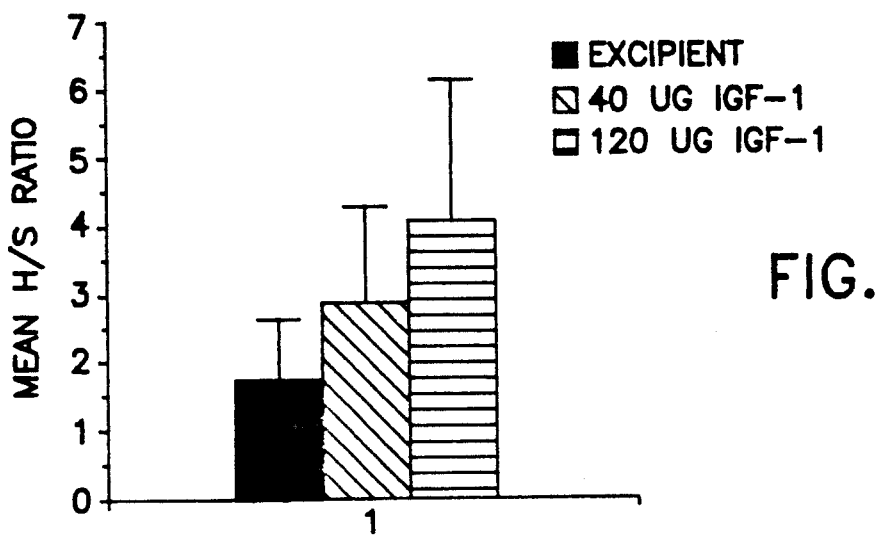
Figure 26A:
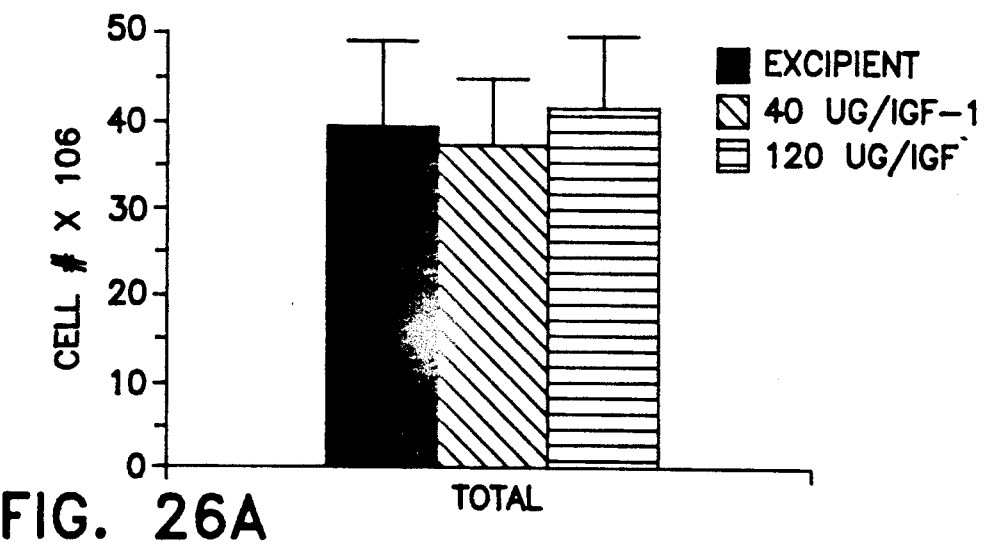
FIGS. 26A, 26B, and 26C show graphs of total splenocyte number, T-cell subpopulations and splenic B-cell number, respectively, 21 days after irradiation of mice with transplanted bone marrow and treated with excipient, 40 $\mu g$ IGF-I, or 120 $\mu g$ IGF-I.
Figure 26B:
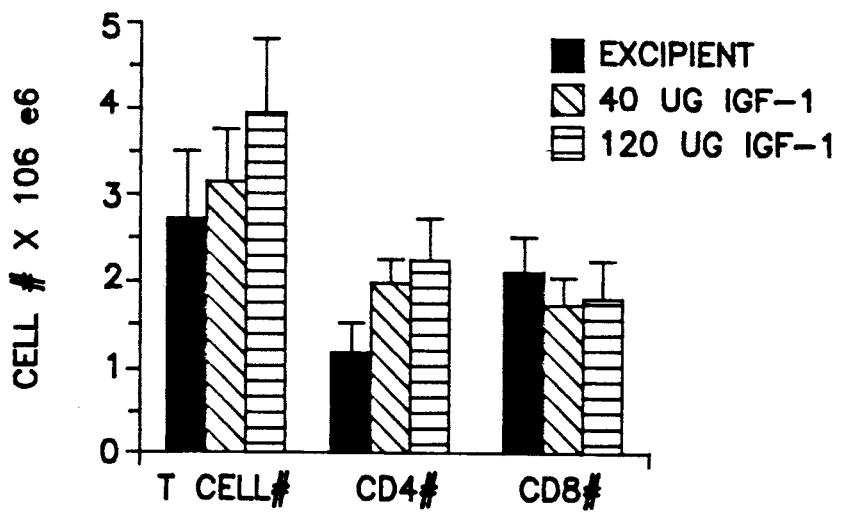
Figure 26C:
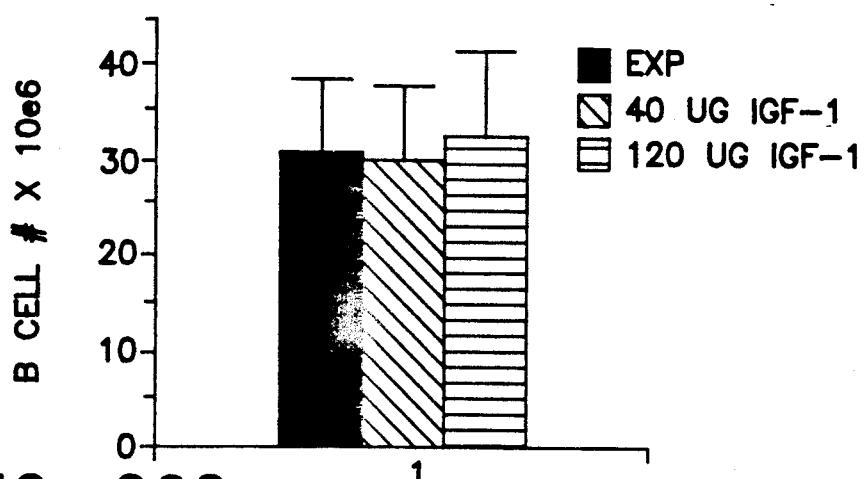
Figure 27A:
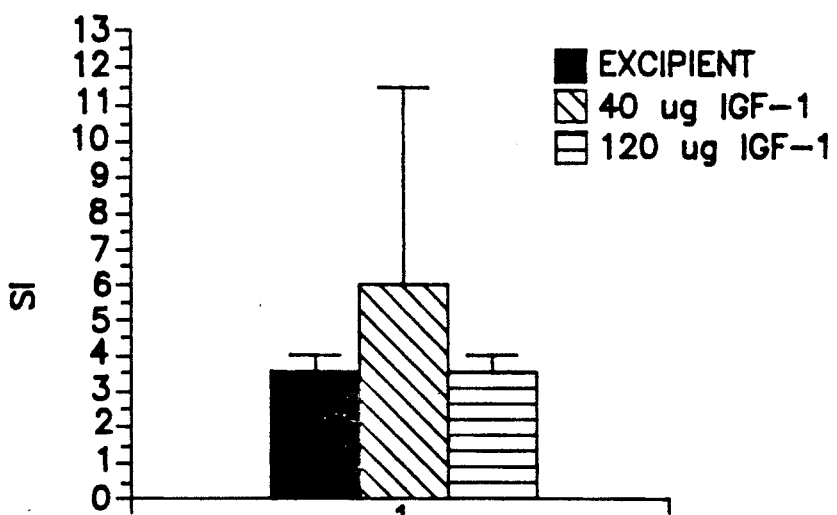
FIG. 27 represents a graph of the mitogenic responses 21 days after irradiation of mice with transplanted bone marrow and treated with excipient, 40 $\mu g$ IGF-I, or 120 $\mu g$ IGF-I using the mitogens LPS (FIG. 27A), Con A (FIG. 27B), or PWM (FIG. 27C).
Figure 27B:
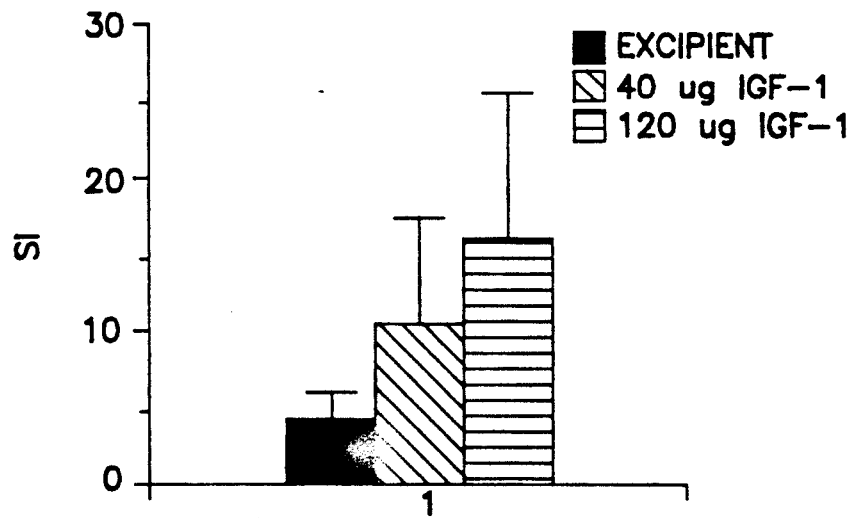
Figure 27C:
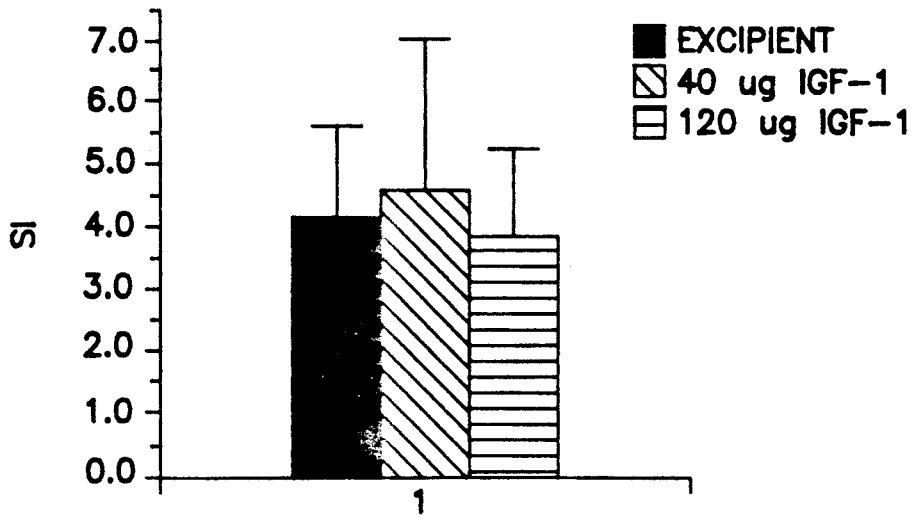

When examined at 21 days post irradiation, IGF-I again induced an alteration in the peripheral blood lymphocytes $CD_4:CD_8$ ratio due to increases in the $CD_+$T-cell population (FIG. 25). By this time, total splenocyte numbers in the IGF-I-treated groups had returned to control values but a slight increase was still measurable in the splenic $CD_4$+T cell population (FIG. 26). This increase in T-cells was reflected in increased mitogenic responsiveness. Con A stimulation of splenic T-cells tripled in the high-dose IGF-I-treated mice (FIG. 27).

B-cell mitogenic responses to LPS were unaffected by IGF-I treatment when examined at this time point.

Surprisingly, the thymic lymphocyte numbers of the high- and low-dose IGF-I-treated mice were still dramatically increased compared to controls (FIG. 28).

Taken together with the increases in splenic $CD_4$ number and Con A responsiveness, these data suggest that IGF-I increases the rate of peripheral cell repopulation and supports an important therapeutic role for this molecule following syngenic bone marrow transplantation.

EXAMPLE IV

IGF-I Administration to Man

This clinical investigation provides evidence that IGF-I also affects the immune system of a human.

I. Protocol

A Phase I clinical study was conducted of the safety and pharmacokinetics following repeat administration (multidose) of IGF-I in healthy adult males. Twelve human patients received a bolus injection of 0.03 mg/kg rhIGF-I as described above each morning for five consecutive days. On screening and ten hours post bolus on day five, blood samples were taken for determination of hematology.

II. Results

It was found that the hemoglobin, hematocrit, and red blood cells (RBCs) were significantly lower on day 5 as compared to screening or post-treatment week 2 ($p=0.001$, 0.0004, 0.0005, and 0.0005). In contrast, the white blood cells (WBCs) increased significantly from screening to day 5 (from $6.1\pm1.5$ to $7.5\pm1.9$ M/CMM, $p=0.0018$). Furthermore, at post-treatment week 2 the WBCs fell significantly from the value at day 5 (from $7.5\pm1.9$ to $6.4\pm1.6$M/CMM, $p=0.003$), so that the pretreatment and 2-week post-treatment WBC values were not significantly different.

Therefore, despite the RBCs falling in this study, the WBCs rose. It is known that 25 to 30% of the white blood cells are lymphocytes. The 23% increase in the total number of WBCs in the blood of the IGF-I-treated subjects makes it very likely that there was also an increase in the number of lymphocytes following this course of IGF-I treatment in man. Compare FIG. 22B, which shows statistically significant changes in the peripheral blood CD. +lymphocytes number in mice after treatment with 120 μg IGF-I. See also Table III on the increased effects of the combination of des-IGF-I and bGH on lymphocyte number and WBCs in aged rats.

CONCLUSION

IGF-I was isolated and named first as a "somatomedin" to indicate that it mediated the whole-body growth-promoting activity of GH. It was later named IGF-I in recognition of its insulin-like metabolic activities. It is therefore surprising that IGF-I, a molecule considered to be a metabolic regulator of somatic growth, was shown to have growth factor activity on cells of the immune system similar to that of many of the interleukins.

It is known that GH receptors, IGF-I receptors, and insulin receptors are present on cells of the immune system. The functional effect in vivo of these receptors and the activity of their ligands on the immune system was unknown until the present invention. The effects of insulin and GH on the immune system have been taken to be insignificant. See, e.g., Snow, *J. Immunol.*, 135:776-778 (1985). Most tissues in the body have receptors for GH. IGF-I, and insulin where these hormones act to regulate the basic metabolic functions of cells, for example, glucose uptake or amino acid transport. The receptors that have been demonstrated to be present in immune tissue could function to control these activities, rather than act to influence their differentiation, growth, and the immunological activities. Recent literature has recognized that the role of IGF-I in affecting immune cytology or function is unknown. See Fu et al., *J. Immunol.,* 146: 1602-1608 (1991).

It is well recognized that aged, underfed, or malnourished patients, or patients suffering from illnesses or diseases, become immune deficient. It is additionally known that these patients also become IGF-I deficient. The findings herein suggest that this immune deficiency is directly related to, and exacerbated by, if not caused by, this IGF-I deficiency. Restoring IGF-I blood concentrations in patients would be expected to result in an amelioration of their immune deficiency. IGF-I dramatically affects the size of the thymus in several animal models. Thymic growth has been seen in hypophysectomized and dwarf rats, in young, adult, and aged rats, in mice, and in rabbits. The thymus involutes with age in most animals; it reaches a maximal size and then begins involuting in man after puberty. This involution is associated with a decline in the activity of the immune system. This invention therefore provides in one aspect a means of stimulating the immune system of an aged human to restore the thymic tissue to that of a much younger person. The combination of an agent that has anabolic activity on the major internal organs, with improvement of hematology and immune function, makes IGF-I an attractive drug for treating adult or aged humans. The ability to rejuvenate the thymus and therefore boost the immune system is seen as providing a range of therapeutic opportunities.

Such opportunities include common varied agammaglobulinemia in which B-cells fail to mature into Ig secretory cells and the serum contains less than 250 mg/dl compared to 1000 mg/dl that is the normal concentration. IGF-I produced significant increases in serum Ig levels (FIG. 20) and may be useful in this disease.

A further use of the invention would be to administer the IGF-I to a patient who suffers from a hereditary illness that results in an impaired immune system. An example of such a patient would be a child suffering from congenital thymic aplasia (diGeorge syndrome) in which the thymus is atrophied and T-cells are severely diminished, leading to opportunistic infections that are often fatal. The reason for this disease is unknown. IGF-I might be expected to give an improved size, cellularity, and responsiveness of the thymus in these patients. The course of treatment would be intermittent, with, for example, a predicted 14-day period of treatment being given followed by a resting period of more than 21 days between exposures to IGF-I. At this time, the cell counts in the immune tissues would have returned to normal, but their ability to response to mitogens or to produce antibodies would be enhanced. Such an intermittent course of treatment of producing waves of cellular development would be sustainable and lead to a long-term restoration of immune function in hereditary conditions of the DiGeorge type.

A third opportunity is acquired immunodeficiency syndrome (AIDS). Patients with AIDS have no T-cell immunity and inversed T4/T8 ratios. IGF-I has been shown to increase T-cell mitogen responsiveness and specifically enhance CD$_4$+cell number (FIGS. 5, 10, 11) and as such may be a useful drug in the treatment of AIDS.

The data set forth above suggests that administration of IGF-I is beneficial to increase immunoglobulin production in patients suffering from insufficient immunoglobulin production. The interval between immunizations might be expected to be reduced by the invention herein. The more rapid proliferation of cells in vitro from IGF-I-treated mice suggested that enhanced antibody responses could be achieved more rapidly. This would allow more compressed immunization protocols. For example, in man it is common to give primary, secondary, and tertiary immunizations separated by many months. During this time the patient is at risk of exposure to the agent from which he or she is being protected. It would an advantage to reduce the interval between immunizations by using IGF-I to boost the immune system so that the above risk could therefore be reduced.

Another use of the invention is to give a patient a course of IGF-I treatment during his or her recovery from major illnesses or following surgery when an infection or relapse might be expected. An enhanced immune response would be expected to aid such a patient to mount an immune challenge to the infection or relapse.

In the above examples, the effectiveness of IGF-I has been demonstrated as follows: (1) in three species (mouse, rat, and rabbit); (2) in both sexes (male and female rats); and (3) in several animal models, including animals made surgically GH and IGF-I deficient (hypophysectomized rats), animals with hereditary GH and IGF-I deficiency (dwarf rats), normal animals (ovariectomized rats), normally aged animals that are IGF-I deficient (18-month-old rats), animals showing accelerated aging (retired breeder mice), and animals with reduced immune function (the aged animals).

It does not necessarily follow from the above studies that a minimum of 14 days of IGF-I treatment is needed to induce the changes observed. In the mouse 14-day treatment was chosen as this proved reliable of inducing immune tissue responses. It is possible that 7 days of IGF-I treatment, which did induce an increase in cell number, would eventually lead to functionally active mature lymphocytes. Additionally, less than 7 days of treatment (for example, the 5 days used in Example IV in man) might also be an effective period of administration. Furthermore, IGF-I treatment by injections rather than continuous infusion is also expected to be efficacious.

It would be reasonably expected that the rabbit, rat, and mice data herein may be extrapolated to avians, horses, cows, and other mammals, correcting for the body weight of the avian or mammal in accordance with recognized veterinary and clinical procedures. Humans are believed to respond in this manner as well. IGF-I receptors have been demonstrated on human lymphocytes [Kozak et al., *Cell Immunol.*, 109:318 (1987)], and evidence of similar responses in man is demonstrated in Example IV. Thus, it would be reasonably expected that in man IGF-I would have a beneficial restorative effect on immune function in all patients.

What is claimed is:

1. A method for stimulating a mammal's or avian's antibody-mediated immune system comprising administering to the mammal or avian an immune-stimulating effective amount of IGF-I.

2. The method of claim 1 wherein the mammal is a human.

3. The method of claim 2 wherein the human is an aged human.

4. The method of claim 2 wherein the human has a compromised immune system.

5. A method for stimulating the antibody-mediated immune system of a human having AIDS comprising administering to the human an immune-stimulating effective amount of IGF-I.

6. The method of claim 1 wherein the mammal has undergone a bone marrow transplant.

7. The method of claim 2 wherein the effective amount of IGF-I is 0.01 to 1 mg/kg/day.

8. The method of claim 1 further comprising administering growth hormone to the mammal or avian in an effective amount.

9. A method of claim 8 wherein the growth hormone is human growth hormone and the effective amount is at least 0.1 mg/kg/day.

10. A method for increasing a mammal's or avian's antibody response to an immunogen comprising administering to the mammal or avian the immunogen and an effective amount of IGF-I.

11. The method of claim 10 wherein the administration is concurrent and wherein the immunogen is a virus or a bacterium and further administering a boost of the immunogen to the mammal or avian.

12. The method of claim 11 wherein the immunogen is a vaccine.

13. A method of increasing the amount of immunoglobulin produced by B-cells of a human or other mammalian subject in response to an immunogen, where said subject suffers from a condition in which insufficient immunoglobulin production occurs, comprising administering to the subject an effective amount of IGF-I, the amount being effective to increase the production of immunoglobulin.

14. A method of increasing the T-cell responsiveness in a human or other mammalian subject in response to an immunogen, where said subject suffers from a condition in which insufficient T-help or T-cytolytic activity occurs, comprising administering to the subject an effective amount of IGF-I, the amount being effective to increase the T-help or T-cytolytic activity.

15. The method of claim 14 wherein the immunogen is a virus or a tumor.

16. A method of treating an immune-deficient mammal comprising:
 (a) measuring the serum IGF-I level of the mammal; and
 (b) administering to the mammal an effective amount of IGF-I to restore antibody-mediated immunity in the mammal.

* * * * *

UNITED STATES PATENT AND TRADEMARK OFFICE
Certificate

Patent No. 5,202,119                                                                                 Patented: April 13, 1993

On petition requesting issuance of a certificate for correction of inventorship pursuant to 35 U.S.C. § 256, it has been found that the above-identified patent, through error and without any deceptive intent, improperly sets forth the inventorship.

Accordingly, it is hereby certified that the correct inventorship of this patent is: Ross G. Clark, Paula M. Jardieu and Kenneth A. Kudsk.

Signed and Sealed this twelfth day of September, 1995.

MICHAEL G. WITYSHYN
                                                                       *Supervisory Patent Examiner*
                                                                  Patent Examining Art Unit 1815